(12) United States Patent
Molt et al.

(10) Patent No.: US 8,877,937 B2
(45) Date of Patent: Nov. 4, 2014

(54) PROCESS FOR PREPARING TRANSITION METAL-CARBENE COMPLEXES

(71) Applicant: BASF SE, Ludwigshafen (DE)

(72) Inventors: Oliver Molt, Hirschberg (DE); Evelyn Fuchs, Mannheim (DE); Martina Egen, Dossenheim (DE); Klaus Kahle, Ludwigshafen (DE); Christian Lennartz, Schifferstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/778,262

(22) Filed: Feb. 27, 2013

(65) Prior Publication Data

US 2013/0178621 A1    Jul. 11, 2013

Related U.S. Application Data

(63) Continuation of application No. 12/162,863, filed as application No. PCT/EP2007/050193 on Jan. 9, 2007, now Pat. No. 8,410,280.

(30) Foreign Application Priority Data

Jan. 31, 2006 (EP) ..................... 06101109

(51) Int. Cl.
    *C07F 15/00* (2006.01)
    *B01J 31/22* (2006.01)
(52) U.S. Cl.
    CPC ......... *C07F 15/0086* (2013.01); *C07F 15/0033* (2013.01); *C07F 15/0073* (2013.01); *B01J 31/2265* (2013.01)
    USPC ........................................................ 548/103
(58) Field of Classification Search
    USPC ........................................................ 548/103
    See application file for complete search history.

(56) References Cited

U.S. PATENT DOCUMENTS

2005/0258742 A1  11/2005  Tsai et al.
2006/0258043 A1  11/2006  Bold et al.

FOREIGN PATENT DOCUMENTS

WO    WO 2005/019373    3/2005
WO    WO 2005/113704    12/2005

OTHER PUBLICATIONS

Coleman, Karl S. et al., "Silver(I) Complex of a New Imino-N-Heterocyclic Carbene and Ligand Transfer to Palladium (II) and Rhodium (I)," Dalton Trans., pp. 2917-2922, XP002309661, (2003).
Simal, Francois et al., "Evaluation of Ruthenium-Based Complexes for the Controlled Radical Polymerization of Vinyl Monomers," Can. J. Chem., vol. 79, pp. 529-535, XP002425066 (2001).
Sajoto, Tissa et al., "Blue and Near-UV Phosphorescence from Iridium Complexes with Cyclometalated Pyrazolyl or N-Heterocyclic Carbene Ligands," Inorganic Chemistry, vol. 44, pp. 7992-8003 (2005).
Dorta Reto et al., "Double C-H Activation in a Rh-NHC Complex Leading to the Isolation of a 14-Electron Rh(III) Complex," J. Am. Chem. Soc., vol. 126, pp. 5054-5055 (2004).

*Primary Examiner* — Joseph Kosack
(74) *Attorney, Agent, or Firm* — Oblon, Spivak, McClelland, Maier & Neustadt, L.L.P.

(57) ABSTRACT

Process for preparing cyclometallated transition metal-carbene complexes comprising at least one carbene ligand, which comprises reacting a ligand precursor with a base, an auxiliary reagent and a metal complex comprising at least one metal $M^1$ (route A) or reacting the ligand precursor with a basic auxiliary reagent and a metal complex comprising at least one metal $M^1$ (route B). The present invention further relates to the use of an auxiliary reagent selected from among salts comprising at least one metal selected from the group consisting of Ag, Hg, Sb, Mg, B and Al together with a base in a process for preparing cyclometallated metal complexes.

19 Claims, No Drawings

PROCESS FOR PREPARING TRANSITION METAL-CARBENE COMPLEXES

REFERENCE TO PRIOR APPLICATIONS

This application is a Continuation of U.S. application Ser. No. 12/162,863, filed Jul. 31, 2008, now allowed U.S. Pat. No. 8,410,280; which is a 371 of PCT/EP07/50193, filed Jan. 9, 2007. Priority to European patent application 06101109.4, filed Jan. 31, 2006, is claimed.

DESCRIPTION

The present invention relates to a process for preparing cyclometallated transition metal-carbene complexes comprising at least one carbene ligand, which comprises reacting a ligand precursor with a base, an auxiliary reagent and a metal complex comprising at least one metal $M^1$ (route A) or reacting the ligand precursor with a basic auxiliary reagent and a metal complex comprising at least one metal $M^1$ (route B). The present invention further relates to the use of an auxiliary reagent selected from among salts comprising at least one metal selected from the group consisting of Ag, Hg, Sb, Mg, B and Al together with a base in a process for preparing cyclometallated metal complexes.

Organic light-emitting diodes (OLEDs) exploit the ability of materials to emit light when they are excited by an electric current. OLEDs are of particular interest as alternatives to cathode ray tubes and liquid crystal displays for producing flat VDUs. Owing to their very compact construction and intrinsically lower power consumption, devices comprising OLEDs are particularly suitable for mobile applications, for example for use in mobile telephones, laptops, etc.

Numerous materials which emit light on excitation by an electric current have been proposed.

WO2005/019373 discloses the use of transition metal complexes comprising at least one carbene ligand in organic light-emitting diodes (OLEDs). These are prepared by deprotonation of the corresponding ligand precursors and subsequent reaction with suitable metal complexes comprising the desired metal without addition of further auxiliary reagents. Here, the yields of the transition metal complexes obtained are sometimes in need of improvement.

The prior art discloses processes in which transition metal-carbene complexes are prepared in the presence of silver-comprising auxiliary reagents. Known processes involve, in particular, the use of $Ag_2O$ for preparing silver-carbene complexes and subsequent carbene transfer to other metals and also the use of silver salts such as $AgBF_4$, $AgCO_2CF_3$, $AgPF_6$, AgOTf for halide abstraction and for anion exchange in metal-carbene complexes.

Mark E. Thompson et al., Inorganic Chemistry, 2005, 44, 7992-8003, describe iridium complexes with cyclometallated N-heterocyclic carbene ligands (NHC). The preparation of iridium complexes bearing three cyclometallated carbene ligands (C^C:) is carried out by reacting the corresponding imidazolium (pmiH$^+$) or benzimidazolium (pmbH$^+$) iodide salts with silver(I) oxide ($Ag_2O$) and iridium(III) chloride hydrate under reflux in 2-ethoxyethanol in one step, giving a mixture of the desired fac- and mer-Ir(C^C:)$_3$ complexex in low yields (according to the description <10%) together with a product of the formula [(C^C:)$_2$IrCl]$_2$. The product of the formula [(C^C:)$_2$IrCl]$_2$ can in turn be reacted with the corresponding imidazolium or benzimidazolium iodide salts and $Ag_2O$ in 1,2-dichloroethane to form fac- and mer-Ir(C^C:)$_3$ complexes in order to increase the yield.

WO2005/113704 relates to luminescent compounds bearing carbene ligands. The compounds can be, inter alia, iridium-(benz)imidazolylidene carbene complexes. In the examples, these are prepared in one step by reacting the corresponding (benz)imidazolium iodide salts with $Ag_2O$ and iridium(III) chloride hydrate. The yields of the desired iridium complexes are low.

Steven P. Nolan et al. J. Am. Chem. Soc. 2004, 126, 5054-5055, describe cyclometallated N-heterocyclic carbene complexes (NHC) of rhodium. According to the description, the doubly cyclometallated complex RhCl(N,N-di(tert-butyl)imidazol-2-ylidene))$_2$ is prepared by reacting [Rh(COE)$_2$Cl]$_2$ with N,N-di(tert-butyl)imidazol-2-ylidene) in benzene. This can, in a further step, be converted into a 14 electron Rh(III) complex by reaction with $AgPF_6$ in $CH_2Cl_2$. The silver salt is used by Steven P. Nolan et al. for the abstraction of Cl$^-$. CH activation is present before the addition of the silver salt.

Alfred F. Noels et al., Can. J. Chem. 79: 529-535 (2001) describe, inter alia, the preparation of the cyclometallated Ru complex RuCl(p-cymene)(triazolinylidene) by stoichiometric reaction of triazolinylidene carbene (1,3,4-triphenyl-4,5-dihydro-1H-1,2,4-triazol-5-ylidene) with the dimeric Ru complex [RuCl$_2$(p-cymene)]$_2$ with addition of an excess of a base (EtN-i-Pr$_2$). The corresponding cationic complex is obtained from this complex by abstraction of Cl$^-$ by means of $AgBF_4$ in acetonitrile. Alfred F. Noels et al. thus use the silver salt, as do Steven P. Nolan et al., for the abstraction of Cl$^-$. CH activation is present before the addition of the silver salt.

It is an object of the present invention to provide a process for preparing cyclometallated carbene complexes, in particular Ir(III)-carbene complexes, in which the complexes are obtained in good yields in a simple reaction procedure.

This object is achieved by a process for preparing cyclometallated carbene complexes of the general formula (I) comprising at least one carbene ligand

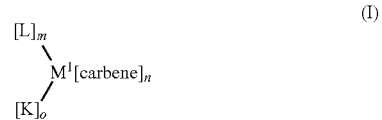

where the symbols have the following meanings:
  $M^1$ is a metal atom selected from the group consisting of Ir, Co, Rh, Ni, Pd, Pt, Fe, Ru, Os, Cr, Mo, W, Mn, Tc, Re, Cu and Au, preferably Ir, Os, Ru, Rh, Pd, Co and Pt, particularly preferably Ir, Pt, Rh and Os, very particularly preferably Ir, in any oxidation state possible for the respective metal atom, more preferably Ir(I) and Ir(III) and in particular Ir(III);
  carbene is a carbene ligand of the general formula (II)

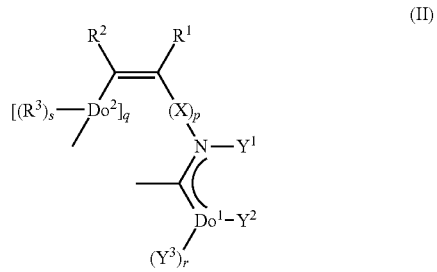

L is a monoanionic or dianionic ligand which may be monodentate or bidentate;

K is an uncharged monodentate or bidentate ligand;

n is the number of carbene ligands, with n being at least 1, preferably at least 2, and the carbene ligands in the complex of the formula I being able to be identical or different in the case of n>1;

m is the number of ligands L, with m being able to be 0 or ≥1 and the ligands L being able to be identical or different in the case of m>1;

o is the number of ligands K, with o being able to be 0 or ≥1 and the ligands K being able to be identical or different in the case of o>1;

where the sum n+m+o is dependent on the oxidation state and coordination number of the metal atom used and on the denticity of the ligands carbene, L and K and also on the charge on the ligands carbene and L, with the proviso that n is at least 1;

where the symbols in the carbene ligand of the general formula II have the following meanings:

Do$^1$ is a donor atom selected from the group consisting of C, P, N, O, S and Si, preferably P, N, O and S, particularly preferably N;

Do$^2$ is a donor atom selected from the group consisting of C, N, P, O and S;

r is 2 when Do$^1$ is C or Si, is 1 when Do$^1$ is N or P and is 0 when Do$^1$ is O or S;

s is 2 when Do$^2$ is C, is 1 when Do$^2$ is N or P and is 0 when Do$^2$ is O or S;

X is a spacer selected from the group consisting of silylene, alkylene, arylene, heteroarylene, alkynylene, alkenylene, NR$^{13}$, PR$^{14}$, BR$^{15}$, O, S, SO, SO$_2$, CO, CO—O, O—CO and (CR$^{16}$R$^{17}$)$_w$, where one or more nonadjacent (CR$^{16}$R$^{17}$) groups can be replaced by NR$^{13}$, PR$^{14}$, BR$^{15}$, O, S, SO, SO$_2$, CO, CO—O, O—CO, preferably alkylene, arylene, alkenylene, silylene, SO or SO$_2$, particularly preferably C$_1$-C$_3$-alkylene, C$_6$-1,2-arylene or C$_2$-alkenylene, where at least one of the carbon atoms of the groups mentioned as spacer may optionally be substituted, for example, by methyl, ethyl, n-propyl or i-propyl groups or by groups having a donor or acceptor action selected from among halogen radicals, preferably F, Cl, Br, particularly preferably F, alkoxy radicals, aryloxy radicals, carbonyl groups, ester groups, amino groups, amide radicals, CHF$_2$, CH$_2$F, CF$_3$, CN, thio groups and SCN, very particularly preferably methylene, ethenylene or 1,2-phenylene;

w is from 2 to 10;

R$^{13}$, R$^{14}$, R$^{15}$, R$^{16}$, R$^{17}$ are each H, alkyl, aryl, heteroaryl, alkenyl, alkynyl;

p is 0 or 1, preferably 0;

q is 0 or 1, preferably 0;

Y$^1$, Y$^2$ are each, independently of one another, hydrogen or a carbon-comprising group selected from the group consisting of alkyl, aryl, heteroaryl, alkynyl and alkenyl groups;

or

Y$^1$ and Y$^2$ together form a bridge between the donor atom Do$^1$ and the nitrogen atom N which has at least two atoms, preferably two or three atoms, particularly preferably two atoms, of which at least one is a carbon atom and the further atoms are preferably nitrogen or carbon atoms, with the bridge being able to be saturated or unsaturated, preferably unsaturated, and the at least two atoms of the bridge being able to be substituted or unsubstituted;

Y$^3$ is hydrogen, an alkyl, aryl, heteroaryl, alkynyl or alkenyl radical, preferably an alkyl, heteroaryl or aryl radical, particularly preferably an alkyl radical;

or

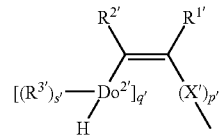

where Do$^{2'}$, q', s', R$^{3'}$, R$^{1'}$, R$^{2'}$, X' and p' independently have the same meanings as Do$^2$, q, s, R$^3$, R$^1$, R$^2$, X and p;

with Y$^3$ and Y$^2$ also being able to be joined to one another via a bridge which can have the following meanings:

alkylene, arylene, heteroarylene, alkynylene, alkenylene, NR$^{25}$, PR$^{26}$, BR$^{27}$, O, S, SO, SO$_2$, SiR$^{32}$R$^{33}$, CO, CO—O, O—CO and (CR$^{28}$R$^{29}$)$_y$, where one or more nonadjacent (CR$^{28}$R$^{29}$) groups may be replaced by NR$^{25}$, PR$^{26}$, BR$^{27}$, O, S, SO, SO$_2$, SiR$^{32}$R$^{33}$, CO, CO—O, O—CO, where y is from 2 to 10;

and

R$^{25}$, R$^{26}$, R$^{27}$, R$^{28}$, R$^{29}$, R$^{32}$, R$^{33}$ are each H, alkyl, aryl, heteroaryl, alkenyl, alkynyl;

R$^1$, R$^2$ are each, independently of one another, hydrogen or an alkyl, aryl, heteroaryl, alkynyl or alkenyl radical, preferably hydrogen, an alkyl radical, a heteroaryl radical or an aryl radical, or R$^1$ and R$^2$ together form a bridge having a total of from three to five atoms, preferably four atoms, of which one or two atoms can be heteroatoms, preferably N, and the remaining atoms are carbon atoms, so that the group

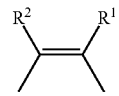

forms a five- to seven-membered, preferably six-membered, ring which may optionally have, in addition to the existing double bond, one further double bond or in the case of a six- or seven-membered ring two further double bonds and may optionally be substituted by alkyl or aryl groups and/or groups having a donor or acceptor action and may optionally comprise at least one heteroatom, preferably N, with preference being given to a six-membered aromatic ring which is unsubstituted or substituted by alkyl or aryl groups, or the preferred six-membered aromatic ring is fused with further rings which may optionally comprise at least one heteroatom, preferably N, preferably six-membered aromatic rings;

with Y$^1$ and R$^1$ also being able to be joined to one another via a bridge which can have the following meanings:

alkylene, arylene, heteroarylene, alkynylene, alkenylene, NR$^{18}$, PR$^{19}$, BR$^{20}$, O, S, SO, SO$_2$, SiR$^{30}$R$^{31}$, CO, CO—O, O—CO and (CR$^{21}$R$^{22}$)$_x$, where one or more nonadjacent (CR$^{21}$R$^{22}$) groups may be replaced by NR$^{18}$, PR$^{19}$, BR$^{20}$, O, S, SO, SO$_2$, SiR$^{30}$R$^{31}$, CO, CO—O, O—CO, where x is from 2 to 10;
and
$R^{18}, R^{19}, R^{20}, R^{21}, R^{22}, R^{30}, R^{31}$
are each H, alkyl, aryl, heteroaryl, alkenyl, alkynyl;
$R^3$ is hydrogen or an alkyl, aryl, heteroaryl, alkynyl or alkenyl radical, preferably hydrogen or an alkyl, heteroaryl or aryl radical;
which comprises reaction of a ligand precursor of the general formula (III)

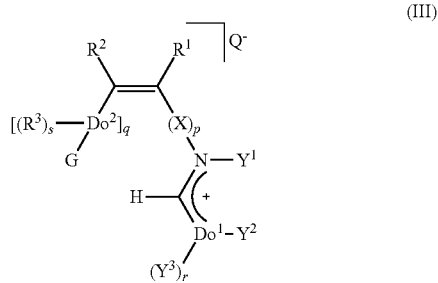

where
$Q^-$ is a monoanionic counterion, preferably halide, pseudohalide, $BF_4^-$, $BPh_4^-$, $PF_6^-$, $AsF_6^-$ or $SbF_6^-$;
and
G is H when $Do^2$=C and
is H or a free electron pair when $Do^2$=N, S, O or P;
and
the further symbols in the ligand precursor of the formula III have the meanings given in respect of the ligand of the formula II,
wherein
the reaction comprises the use of a base and an auxiliary reagent selected from among salts of Ag, Hg, Sb, Mg, B and Al, preferably salts of Ag, (route A) or the use of a basic auxiliary reagent comprising at least one metal selected from the group consisting of Ag, Hg, Sb, Mg, B and Al, preferably Ag, (route B) and the ligand precursor of the general formula III is
(A) reacted with the base, a metal complex comprising at least one metal $M^1$ and the auxiliary reagent (route A), or
(B) reacted with the basic auxiliary reagent to give a protected carbene and the protected carbene is subsequently reacted with a metal complex comprising at least one metal $M^1$ (route B);
to give a cyclometallated metal complex of the formula I.

Preference is given to ligands of the formula II and ligand precursors of the formula III in which p and/or q are 0, i.e. no spacers X and/or no donor atoms $Do^2$ are present in the ligands of the formula II and ligand precursors of the formula III.

The process of the invention makes it possible to prepare cyclometallated transition metal-carbene complexes in good yields in a simple reaction procedure.

For the purposes of the present invention, a bidentate ligand is a ligand which is coordinated at two points to the transition metal atom $M^1$. For the purposes of the present patent application, the term "two-dentate" is used synonymously with the term "bidentate".

For the purposes of the present invention, a monodentate ligand is a ligand which coordinates at one point on the ligand to the transition metal atom $M^1$.

Depending on the coordination number of the metal $M^1$ used and the nature and number of the ligands L, K and carbene used, various isomers of the corresponding metal complexes can be present for the same metal $M^1$ and the same nature and number of the ligands K, L and carbene used. For example, in the case of complexes of a metal $M^1$ having a coordination number of 6 (i.e. octahedral complexes), for example Ir(III) complexes, both cis and trans isomers are possible when the complexes have the general composition $MA_2B_4$ and fac and mer isomers (facial/meridional isomers) are possible when the complexes have the general composition $MA_3B_3$. In the case of square planar complexes of a metal $M^1$ having a coordination number 4, for example Pt(II) complexes, cis and trans isomers are possible when the complexes have the general composition $MA_2B_2$. The symbols A and B are in each case one bonding point of a ligand, with not only monodentate but also bidentate ligands being able to be present. In terms of the abovementioned general composition, an unsymmetrical bidentate ligand has one group A and one group B.

A person skilled in the art will know what cis/trans or fac/mer isomers are. In the case of octahedral complexes, cis isomerism means that in complexes of the composition $MA_2B_4$ the two groups A occupy adjacent corners of an octahedron, while in the case of trans isomerism the two groups A occupy opposite corners of an octahedron. In complexes of the composition $MA_3B_3$, three groups of the same type can occupy either the corners of one octahedral face (facial isomer) or a meridian, i.e. two of the three ligand bonding points are in trans positions relative to one another (meridional isomer). For details regarding the definition of cis/trans isomers or fac/mer isomers in octahedral metal complexes, see, for example, J. Huheey, E. Keiter, R. Keiter, Anorganische Chemie: Prinzipien von Struktur und Reaktivität, 2nd revised edition, translated and expanded by Ralf Steudel, Berlin; New York: de Gruyter, 1995, pages 575, 576.

In the case of square planar complexes, cis isomerism means that in complexes of the composition $MA_2B_2$ both the two groups A and the two groups B occupy adjacent corners of a square, while in the case of trans isomerism both the two groups A and the two groups B in each case occupy the two diagonally opposite corners of a square. For details regarding the definition of cis/trans isomers in square planar metal complexes, see, for example, J. Huheey, E. Keiter, R, Keiter, Anorganische Chemie: Prinzipien von Struktur und Reaktivität, 2nd revised edition, translated and expanded by Ralf Stendel, Berlin; New York: de Gruyter, 1995, pages 557 to 559.

In general, the various isomers of the metal complexes of the formula I can be separated by methods known to those skilled in the art, for example by chromatography, sublimation or crystallization.

The present invention thus relates both to the preparation of individual isomers of the transition metal complexes of the formula I and to the preparation of mixtures of various isomers in any mixing ratio.

The transition metal complexes of the general formula I prepared according to the invention particularly preferably have a metal atom $M^1$ selected from the group consisting of Ir, Os, Rh and Pt, with Os(II), Rh(III), Ir(I), Ir(III) and Pt(II) being preferred. Particular preference is given to using Ir, preferably Ir(I) and Ir(III), very particularly preferably Ir(III).

Suitable monoanionic or dianionic ligands L, preferably monoanionic ligands L, which may be monodentate or bidentate, are the ligands customarily used as monodentate or bidentate monoanionic or dianionic ligands.

Suitable monoanionic monodentate ligands are, for example, halides, in particular Cl⁻ and Br⁻, pseudohalides, in particular CN⁻, cyclopentadienyl (Cp⁻), hydride, alkyl radicals which are bound to the transition metal $M^1$ via a sigma bond, for example $CH_3$, alkylaryl radicals which are bound to the transition metal $M^1$ via a sigma bond, for example benzyl.

Suitable monoanionic bidentate ligands are, for example, acetylacetonate and its derivatives, picolinate, Schiff bases, amino acids, arylazoles, e.g. phenylpyridine, and the further bidentate monoanionic ligands mentioned in WO 02/15645, with acetylacetonate and picolinate being preferred.

Suitable dianionic bidentate ligands are, for example, dialkoxides, dicarbonates, dicarboxylates, diamides, diimides, dithiolates, biscyclopentadienyls, bisphosphonates, bissulfonates and 3-phenylpyrazole.

Suitable uncharged monodentate or bidentate ligands K are preferably selected from the group consisting of phosphines, both monophosphines and bisphosphines; phosphonates, both monophosphonates and bisphosphonates, and derivatives thereof, arsenates, both monoarsenates and bisarsenates, and derivatives thereof; phosphites, both monophosphites and bisphosphites; CO; pyridines, both monopyridines and bispyridines; nitriles, dinitriles, allyl, diimines, nonconjugated dienes and conjugated dienes which form a π complex with $M^1$. Particularly preferred uncharged monodentate or bidentate ligands K are selected from the group consisting of phosphines, both monophosphines and bisphosphines, preferably trialkylphosphines, triarylphosphines or alkylarylphosphines, particularly preferably $PAr_3$, where Ar is a substituted or unsubstituted aryl radical and the three aryl radicals in $PAr_3$ can be identical or different, particularly preferably $PPh_3$, $PEt_3$, $PnBu_3$, $PEt_2Ph$, $PMe_2Ph$, $PnBu_2Ph$; phosphonates and derivatives thereof, arsenates and derivatives thereof, phosphites, CO; pyridines, both monopyridines and bispyridines, with the pyridines being able to be substituted by alkyl or aryl groups; nitriles and dienes which form a π complex with $M^1$, preferably $η^4$-diphenyl-1,3-butadiene, $η^4$-1,3-pentadiene, $η^4$-1-phenyl-1,3-pentadiene, $η^4$-1,4-dibenzyl-1,3-butadiene, $η^4$-2,4-hexadiene, $η^4$-3-methyl-1,3-pentadiene, $η^4$-1,4-ditolyl-1,3-butadiene, $η^4$-1,4-bis(trimethylsilyl)-1,3-butadiene and $η^2$- or $η^4$-cyclooctadiene (each 1,3 and each 1,5), particularly preferably 1,4-diphenyl-1,3-butadiene, 1-phenyl-1,3-pentadiene, 2,4-hexadiene, butadiene, $η^2$-cyclooctene, $η^4$-1,3-cyclooctadiene and $η^4$-1,5-cyclooctadiene. Very particularly preferred uncharged monodentate ligands are selected from the group consisting of $PPh_3$, $P(OPh)_3$, $AsPh_3$, CO, pyridine, nitriles and derivatives thereof. Suitable uncharged monodentate or bidentate ligands are preferably 1,4-diphenyl-1,3-butadiene, 1-phenyl-1,3-pentadiene, 2,4-hexadiene, $η^4$-cyclooctadiene and $η^2$-cyclooctadiene (each 1,3 and each 1,5).

The number n of carbene ligands in uncharged transition metal complexes in which the transition metal atom Ir(III) has a coordination number of 6 is from 1 to 3, preferably 2 or 3, particularly preferably 3. If n is >1, the carbene ligands can be identical or different.

The number n of carbene ligands in transition metal complexes in which the transition metal atom Pt(II) has a coordination number of 4 is 1 or 2, preferably 2. If n is >1, the carbene ligands can be identical or different.

The number m of monoanionic ligands L in the abovementioned case is from 0 to 2, preferably 0 or 1, particularly preferably 0. If m is >1, the ligands L can be identical or different but are preferably identical.

The number o of uncharged ligands K is dependent on whether the coordination number 6 of Ir(III) or 4 of Pt(II) has already been reached by means of the carbene ligands and the ligands L. If, when Ir(III) is used, n is three and three monoanionic bidentate carbene ligands are used, then o is 0 in the abovementioned case. If, when Pt(II) is used, n is two and two monoanionic bidentate carbene ligands are used, then o is likewise 0 in this case.

For the purposes of the present patent application, the following applies to the groups $Y^1$ and $Y^2$:

the substituents of the groups $Y^1$ and $Y^2$ can together form a bridge having a total of from two to four, preferably two or three, atoms of which one or two atoms can be heteroatoms, preferably N, and the remaining atoms are carbon atoms, so that $Y^1$ and $Y^2$ together with this bridge form a five- to seven-membered, preferably five- or six-membered, ring which may optionally have two or in the case of a six- or seven-membered ring three double bonds and may optionally be substituted by alkyl or aryl groups and/or groups having a donor or acceptor action and may optionally comprise heteroatoms, preferably N, with preference being given to a five-membered or six-membered aromatic ring which is unsubstituted or substituted by alkyl or aryl groups and/or groups having a donor or acceptor action, or the preferred five-membered or six-membered aromatic ring is fused with further rings which may optionally comprise at least one heteroatom, preferably N, preferably six-membered aromatic rings.

The group $Y^1$ can be joined to the radical $R^1$ via a bridge which can have the following meanings:

alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, O—CO, where x is from 2 to 10;

and $R^{18}$, $R^{19}$, $R^{20}$, $R^{21}$, $R^{22}$, $R^{30}$, $R^{31}$ are each H, alkyl, aryl, heteroaryl, alkenyl, alkynyl.

When $Y^1$ and $Y^2$ together form a bridge so as to form a five- to seven-membered ring, the linking bridge to the radical $R^1$ can be bound directly to the five- to seven-membered ring or be bound to a substituent of this ring, with direct bonding to the five- to seven-membered ring being preferred. The atom which is directly adjacent to the N atom (in the general formula II) of the five- to seven-membered ring is particularly preferably linked via a bridge to $R^1$ if such a linkage is present (cf., for example, the structures Ill, IIm, IIn, IIo mentioned below). When the five- to seven-membered ring formed by means of a bridge formed from $Y^1$ and $Y^2$ is fused with a further five- to seven-membered ring, the linking bridge can be bound to an atom of the fused-on ring (cf., for example, the structure IIk mentioned below).

Preferred bridged structures are mentioned by way of example below. The bridges shown can also occur in other ligand systems used according to the invention, e.g. in the ligand systems of the formulae IIa to j mentioned below.

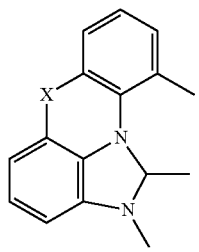

(IIk)

X = O, S, SO, SO$_2$,
CH$_2$CMe$_2$, SiR$^{30}$R$^{31}$, NMe

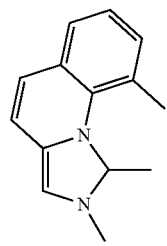

(III)

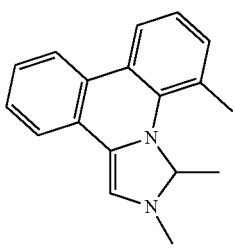

(IIm)

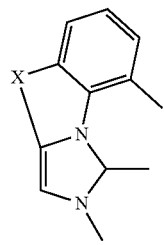

(IIn)

X = O, S, SO, SO$_2$,
CH$_2$CMe$_2$, SiR$^{30}$R$^{31}$, NMe

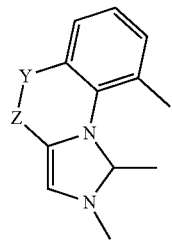

(IIo)

Y-Z = 1x CR$^{21}$R$^{22}$ and 1x O, S,
SO, SO$_2$, CR$^{21}$R$^{22}$, SiR$^{30}$R$^{31}$, NR$^{18}$
or Y-Z =
CO—O, O—CO The radicals R$^{18}$, R$^{20}$, R$^{21}$, R$^{30}$ and R$^{31}$ have been defined above.

For the purposes of the present patent application, the terms aryl radical or group, heteroaryl radical or group, alkyl radical or group and alkenyl radical or group and alkynyl radical or group have the following meanings:

An aryl radical (or group) is a radical which has a basic skeleton of from 6 to 30 carbon atoms, preferably from 6 to 18 carbon atoms, and is made up of an aromatic ring or a plurality of fused aromatic rings. Suitable basic skeletons are, for example, phenyl, naphthyl, anthracenyl or phenanthrenyl. This basic skeleton can be unsubstituted (i.e. all carbon atoms which are substitutable bear hydrogen atoms) or be substituted at one, more than one or all substitutable positions of the basic skeleton. Suitable substituents are, for example, alkyl radicals, preferably alkyl radicals having from 1 to 8 carbon atoms, particularly preferably methyl, ethyl or i-propyl, aryl radicals, preferably C$_6$-aryl radicals which may in turn be substituted or unsubstituted, heteroaryl radicals, preferably heteroaryl radicals comprising at least one nitrogen atom, particularly preferably pyridyl radicals, alkenyl radicals, preferably alkenyl radicals having one double bond, particularly preferably alkenyl radicals having one double bond and from 1 to 8 carbon atoms, or groups having a donor or acceptor action. Suitable groups having a donor or acceptor action are mentioned below. The aryl radicals very particularly preferably bear substituents selected from the group consisting of methyl, F, Cl, CN, aryloxy and alkoxy. The aryl radical or the aryl group is preferably a C$_6$-C$_{18}$-aryl radical, particularly preferably a C$_6$-aryl radical, which may optionally be substituted by at least one of the abovementioned substituents. The C$_6$-C$_{18}$-aryl radical, preferably C$_6$-aryl radical, particularly preferably has one or two of the abovementioned substituents. In the case of a C$_6$-aryl radical, the one substituent is located in the ortho, meta or para position relative to the further point of linkage of the aryl radical, and in the case of two substituents, these can each be located in the meta position or ortho position relative to the further point of linkage of the aryl radical or one radical is located in the ortho position and one radical is located in the meta position or one radical is located in the ortho or meta position and the further radical is located in the para position.

A heteroaryl radical or a heteroaryl group is a radical which differs from the abovementioned aryl radicals in that at least one carbon atom in the basic skeleton of the aryl radical has been replaced by a heteroatom. Preferred heteroatoms are N, O and S. Very particular preference is given to one or two carbon atoms of the basic skeleton of the aryl radical being replaced by heteroatoms. In particular, the basic skeleton is selected from among electron-rich systems such as pyridine and five-membered heteroaromatics such as pyrrole, furan, pyrazole, imidazole, thiophene. The basic skeleton can be substituted on one, more than one or all substitutable positions of the basic skeleton. Suitable substituents are the same ones which have been mentioned above in respect of the aryl groups.

An alkyl radical or an alkyl group is a radical having from 1 to 20 carbon atoms, preferably from 1 to 10 carbon atoms, particularly preferably from 1 to 8 carbon atoms. This alkyl radical can be branched or unbranched and may optionally be interrupted by one or more heteroatoms, preferably Si, N, O or S, particularly preferably N, O or S. Furthermore, this alkyl radical can be substituted by one or more of the substituents mentioned in respect of the aryl groups. It is likewise possible for the alkyl radical to bear one or more aryl groups. In this case, all of the abovementioned aryl groups are suitable. The alkyl radicals are particularly preferably selected from the group consisting of methyl and isopropyl.

An alkenyl radical or an alkenyl group is a radical which corresponds to the abovementioned alkyl radicals having at least two carbon atoms with the difference that at least one C—C single bond of the alkyl radical has been replaced by a C—C double bond. The alkenyl radical preferably has one or two double bonds.

An alkynyl radical or an alkynyl group is a radical which corresponds to the abovementioned alkyl radicals having at least two carbon atoms with the difference that at least one C—C single bond of the alkyl radical has been replaced by a C—C triple bond. The alkynyl radical preferably has one or two triple bonds.

For the purposes of the present application, the terms alkylene, arylene, heteroarylene, alkynylene and alkenylene have the meanings given for the alkyl, aryl, heteroaryl, alkynyl and alkenyl radicals with the difference that the alkylene, arylene, heteroarylene, alkynylene and alkenylene groups have two points of bonding to atoms of the ligand of the formula II.

A bridge which is formed by $Y^1$ and $Y^2$ and has at least two atoms of which at least one is a carbon atom and the further atoms are preferably nitrogen or carbon atoms, with the bridge being able to be saturated or preferably unsaturated and the at least two atoms of the bridge being able to be substituted or unsubstituted, is preferably one of the following groups:

A bridge which has two carbon atoms or one carbon atom and a nitrogen atom and in which the carbon atoms or a carbon atom and a nitrogen atom are joined to one another by a double bond so that the bridge has one of the following formulae, with the bridge preferably having two carbon atoms:

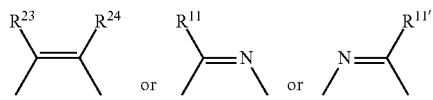

$R^{23}$, $R^{24}$, $R^{11}$ and $R^{11'}$ are each, independently of one another, hydrogen, alkyl, heteroaryl, alkenyl, alkynyl, aryl or a substituent having a donor or acceptor action, or $R^{23}$ and $R^{24}$ together form a bridge having a total of from 3 to 5, preferably 4, atoms of which one or two atoms may optionally be heteroatoms, preferably N, and the remaining atoms are carbon atoms so that this group forms a 5- to 7-membered, preferably six-membered, ring which may optionally have, in addition to the existing double bond, one or in the case of a six- or seven-membered ring two further double bonds and may optionally be substituted by alkyl or aryl groups and/or groups having a donor or acceptor action. A six-membered aromatic ring is preferred. This can be unsubstituted or substituted by alkyl or aryl groups and/or groups having a donor or acceptor action. It is also possible for one or more further aromatic rings to be fused onto this, preferably six-membered, aromatic ring. Any conceivable fusion is possible here. These fused-on radicals can in turn be substituted, preferably by the radicals mentioned in the general definition of the aryl radicals.

A bridge which has two carbon atoms and in which the carbon atoms are joined to one another by a single bond so that the bridge has the following formula:

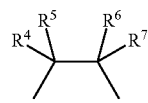

where $R^4$, $R^5$, $R^6$ and $R^7$ are each, independently of one another, hydrogen, alkyl, heteroaryl, alkenyl, alkynyl, aryl or a substituent having a donor or acceptor action, preferably hydrogen, alkyl or aryl.

For the purposes of the present patent application, a group or a substituent having a donor or acceptor action is one of the following groups:

groups having a donor action are groups which have a +I and/or +M effect, and groups having an acceptor action are groups having a –I and/or –M effect. Suitable groups having a donor or acceptor action are halogen radicals, preferably F, Cl, Br, particularly preferably F, alkoxy radicals, aryloxy radicals, carbonyl radicals, ester radicals, both oxycarbonyl and carbonyloxy, amine radicals, amide radicals, $CH_2F$ groups, $CHF_2$ groups, $CH_2F$ groups, $CF_3$ groups, CN groups, thio groups, sulfonic acid groups, sulfonic ester groups, boronic acid groups, boronic ester groups, phosphonic acid groups, phosphonic ester groups, phosphine radicals, sulfoxide radicals, sulfonyl radicals, sulfide radicals, nitro groups, OCN, borane radicals, silyl groups, stannate radicals, imino groups, hydrazine radicals, hydrazone radicals, oxime radicals, nitroso groups, diazo groups, phosphine oxide groups, hydroxy groups or SCN groups. Very particular preference is given to F, Cl, CN, aryloxy and alkoxy.

The group

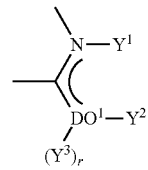

is preferably selected from the group consisting of

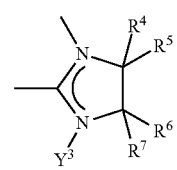

a b

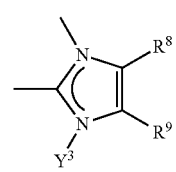

c

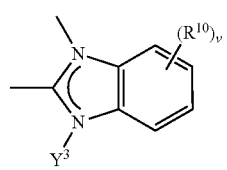

d

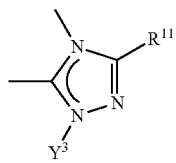

and e

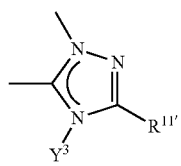

where the symbols have the following meanings:

$R^4, R^5, R^6,$
$R^7, R^8, R^9, R^{11}$
and $R^{11'}$ are each hydrogen, alkyl, aryl, heteroaryl, alkynyl or alkenyl or a substituent having a donor or acceptor action, preferably hydrogen, alkyl, heteroaryl or aryl;

$R^{10}$ is alkyl, aryl, heteroaryl, alkynyl or alkenyl or 2 radicals $R^{10}$ together form a fused-on ring which may optionally comprise at least one heteroatom, preferably N, with preference being given to 2 radicals $R^{10}$ together forming a fused-on aromatic $C_6$ ring onto which, preferably six-membered aromatic ring one or more further aromatic rings may optionally be fused, in which case any conceivable fusion is possible and fused-on radicals may in turn be substituted; or $R^{10}$ is a radical having a donor or acceptor action;

with $R^4$ or $R^5$ in the group a, $R^8$ in the group b, one of the radicals $R^{10}$ in the group c and $R^{11}$ in the group d also being able to be linked to $R^1$ via a bridge which can have the following meanings:

alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups can be replaced by $NR^{18}$, $PR^{19}$, $BR^{20}$, O, S, SO, $SO_2$, $SiR^{30}R^{31}$, CO, CO—O, O—CO, where x is from 2 to 10;

and $R^{18}, R^{19}, R^{20}, R^{21}, R^{22}, R^{30}, R^{31}$ are each H, alkyl, aryl, heteroaryl, alkenyl, alkynyl where, with examples concerning preferred suitable bridges being shown above (see formulae IIk to o);

v is from 0 to 4, preferably 0, 1 or 2, very particularly preferably 0, where, when v is 0, the four carbon atoms of the aryl radical in formula c which may optionally be substituted by $R^{19}$ bear hydrogen atoms;

$Y^3$ is hydrogen, an alkyl, aryl, heteroaryl, alkynyl or alkenyl radical, preferably an alkyl, heteroaryl or aryl radical, particularly preferably an alkyl radical;

or

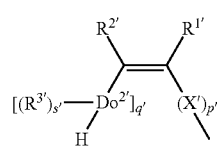

where $Do^{2'}, q', s', R^{3'}, R^{1'}, R^{2'}, X'$ and $p'$ independently have the same meanings as $Do^2, q, s, R^3, R^1, R^2, X$ and $p$.

The group

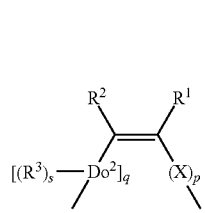

of the carbene ligand of the formula II preferably has the structure

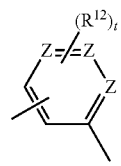

where the symbols have the following meanings:

Z is CH or N, where from 0 to 3, preferably from 0 to 2, particularly preferably 0 or 1, of the symbols Z can be N and if 1 symbol Z is N, Z can be located in the o, m or p position, preferably in the o or p position, relative to the point of linkage of the group to the group

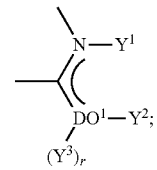

$R^{12}$ is an alkyl, aryl, heteroaryl, alkynyl, alkenyl radical, preferably an alkyl or aryl radical, or 2 radicals $R^{12}$ together form a fused-on ring which may optionally comprise at least one heteroatom, preferably N, with preference being given to 2 radicals $R^{12}$ together forming a fused-on aromatic $C_6$ ring onto which, preferably six-membered aromatic ring one or more further aromatic rings may optionally be fused, with any conceivable fusion being possible and the fused-on radicals in turn being able to be substituted; or $R^{12}$ is a radical having a donor or acceptor action;

with the group of the structure

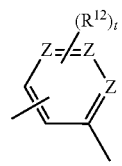

also being able to be linked via the aromatic basic skeleton or via one of the radicals $R^{12}$ to $Y^1$ via a bridge which can have the following meanings:

alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, O—CO, where x is from 2 to 10;
and
$R^{18}, R^{19}, R^{20}, R^{21}, R^{22}, R^{30}, R^{31}$
are each H, alkyl, aryl, heteroaryl, alkenyl, alkynyl;
t is from 0 to 4, where, when t is >1, the radicals $R^{12}$ can be identical or different, and t is preferably 0 or 1 and when t is 1 the radical $R^{12}$ is located in the ortho, meta or para position relative to the point of linkage to the spacer X or when p is 0, to the point of linkage to the nitrogen atom adjacent to the carbene carbon.

In the carbene ligands of the formula II, $Y^3$ can be identical to or different from the above-defined group and have the following meanings which have already been mentioned above:

hydrogen, an alkyl, aryl, heteroaryl, alkynyl or alkenyl radical, preferably an alkyl, heteroaryl or aryl radical or

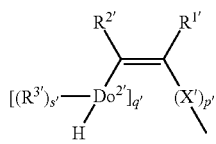

where $Do^{2'}$, q', s', $R^{3'}$, $R^{1'}$, $R^{2'}$, X' and p' independently have the same meanings as $Do^2$, q, s, $R^3$, $R^1$, $R^2$, X and p.

Apart from carbene ligands of the formula II in which the group of the formula

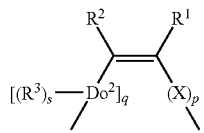

is the structure

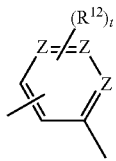

and $Y^3$ is

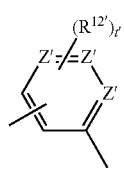

where Z' can have the meanings given for Z, further suitable carbene ligands are ones in which the group of the formula

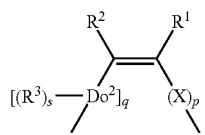

is the structure

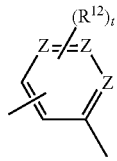

and $Y^3$ is hydrogen or an alkyl, aryl, heteroaryl or alkenyl radical, preferably an alkyl, heteroaryl or aryl radical, particularly preferably an alkyl radical.

The definitions of the symbols correspond to the above-mentioned definitions.

The at least one carbene ligand of the formula II is very particularly preferably selected from the group consisting of

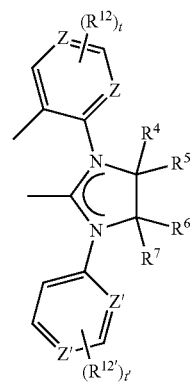

a

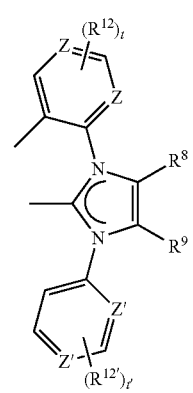

b c
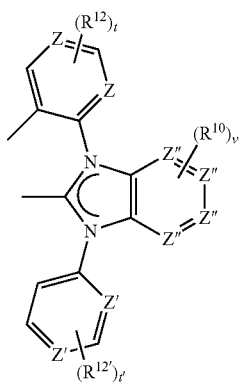

d
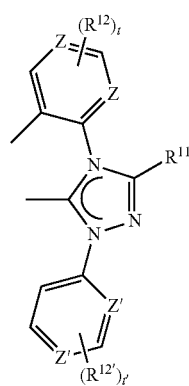

e
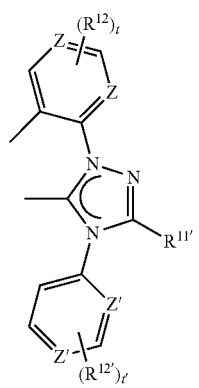

f
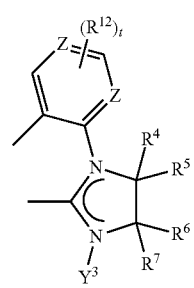

g
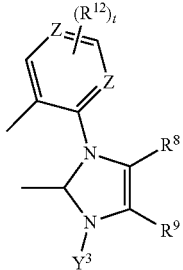

h
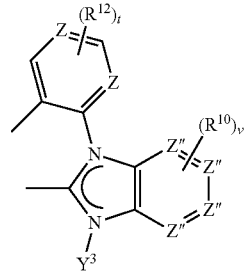

i
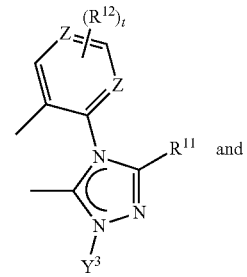
and j
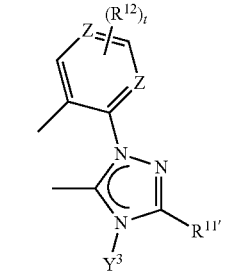

where the symbols have the following meanings:

Z, Z', Z" are identical or different and are each CH or N, where in the case of Z: from 0 to 2 of the symbols Z can be N, preferably 0 or 1, and Z in the case of 1 symbol Z being N can be located in the o or p position, preferably in p position, relative to the point of linkage of the group to the group

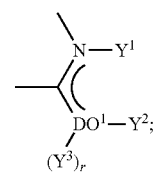

in the case of Z': from 0 to 2 of the symbols Z' can be N, preferably 0 or 1, and Z' in the case of 1 symbol Z' being N can be located in the o or p position, preferably in p position, relative to the point of linkage of the group to the group

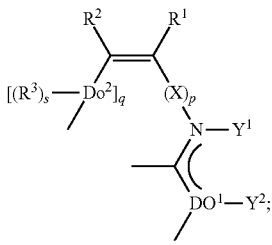

in the case of Z″: from 0 to 4 of the symbols Z″ can be N, preferably from 0 to 3, particularly preferably from 0 to 2, very particularly preferably 0 or 1;

$R^{12}$, $R^{12'}$ are identical or different and are each an alkyl, aryl, heteroaryl, alkynyl or alkenyl radical, preferably an alkyl or aryl radical, or 2 radicals $R^{12}$ or $R^{12'}$ together form a fused-on ring which may optionally comprise at least one heteroatom, preferably N, with preference being given to 2 radicals $R^{12}$ or $R^{12'}$ together forming a fused-on aromatic $C_6$ ring onto which, preferably six-membered aromatic ring one or more further aromatic rings may optionally be fused, with any conceivable fusion being possible and the fused-on radicals in turn being able to be substituted; or $R^{12}$ or $R^{12'}$ is a radical having a donor or acceptor action;

t and t′ are identical or different and are each from 0 to 4, where, when t or t′ is >1, the radicals $R^{12}$ or $R^{12'}$ can be identical or different, and t or t′ is preferably 0 or 1 and when t or t′ is 1 the radical $R^{12}$ or $R^{12'}$ is located in the ortho, meta or para position relative to the point of linkage to the nitrogen atom adjacent to the carbene carbon;

$R^4$, $R^5$, $R^6$, $R^7$, $R^8$, $R^9$, $R^{11}$ and $R^{11'}$ are each hydrogen, alkyl, aryl, heteroaryl, alkynyl or alkenyl or a radical having a donor or acceptor action, preferably hydrogen, alkyl, heteroaryl or aryl;

$R^{10}$ is alkyl, aryl, heteroaryl, alkynyl or alkenyl, preferably alkyl, heteroaryl or aryl, or 2 radicals $R^{10}$ together form a fused-on ring which may optionally comprise at least one heteroatom, preferably N, with preference being given to 2 radicals $R^{10}$ together forming a fused-on aromatic $C_6$ ring onto which, preferably six-membered aromatic ring one or more further aromatic rings may optionally be fused, with any conceivable fusion being possible and the fused-on radicals in turn being able to be substituted; or $R^{10}$ is a radical having a donor or acceptor action;

with the group of the structure

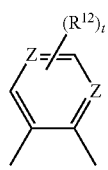

also being able to be joined via the aromatic basic skeleton or via one of the radicals $R^{12}$ to $R^4$ or $R^5$ or the carbon atom to which $R^4$ and $R^5$ are bound in the groups a and f, $R^8$ or the carbon atom to which $R^8$ is bound in the groups b and g, one of the radicals $R^{10}$ or one of the carbon atoms to which $R^{10}$ is bound in the groups c and h and $R^{11}$ or the carbon atom to which $R^{11}$ is bound in the groups d and i via a bridge which can have the following meanings:

alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, O—CO, where x is from 2 to 10;
and
$R^{18}$, $R^{19}$, $R^{20}$, $R^{21}$, $R^{22}$, $R^{30}$, $R^{31}$
are each H, alkyl, aryl, heteroaryl, alkenyl, alkynyl where in the cases in which the group of the structure

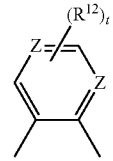

is linked via a bridge to the carbon atom to which $R^4$ and $R^5$ are bound (groups a and f), the carbon atom to which $R^8$ is bound (groups b and g), one of the carbon atoms to which $R^{10}$ is bound (groups c and h) or the carbon atom to which $R^{11}$ is bound (groups d and i), and the respective radical $R^4$ or $R^5$, $R^8$, one of the radicals $R^{10}$ and $R^{11}$ is replaced by a bond to the bridge;

v is from 0 to 4, preferably 0, 1 or 2, very particularly preferably 0, where, when v is 0, the four carbon atoms of the aryl radical in formulae c and h which may optionally be substituted by $R^{10}$ bear hydrogen atoms;

$Y^3$ is hydrogen, an alkyl, aryl, heteroaryl, alkynyl or alkenyl radical, preferably an alkyl, heteroaryl or aryl radical, particularly preferably an alkyl radical.

The transition metal complexes of the formula I prepared by means of the process of the invention can, if a metal atom $M^1$ having a coordination number of 6 is used, be present as the facial or meridional isomer or an isomer mixture of facial and meridional isomers in any ratios if they have a composition $MA_3B_3$, as described above. For example, facial and meridional isomers of the transition metal complex of the formula I are possible when n is 3 and m and o are each 0. When the transition metal complexes of the formula I have a composition $MA_2B_4$, the transition metal complexes can be present in the form of cis/trans isomers in any ratios, as described above. Cis/trans isomers of complexes of the formula I are possible, for example, when $M^1$ is a metal atom having a coordination number of 6 and n is 2 and m is 2, with the two monodentate ligands L being identical, and o is 0 or o is 2 and the two monodentate ligands K are identical and m is 0.

In the case of uncharged transition metal complexes in which the transition metal atom Ir(III) has a coordination number of 6, the number of preferred monoanionic bidentate carbene ligands n is at least 1 and not more than 3. The number of preferred monoanionic bidentate carbene ligands is preferably 2 or 3, particularly preferably 3. In the case of n>1, the carbene ligands can be identical or different.

The transition metal complexes of the formula I can, if a metal atom $M^1$ which has a coordination number of 4 and forms square planar complexes, be present as the cis or trans isomer or as an isomer mixture of cis and trans isomers in any ratios if they have a composition MA$_2$B$_2$, as described above. For example, cis/trans isomers of the transition metal complexes of the formula I are possible when n is 2 and m and o are each 0.

In the case of uncharged transition metal complexes in which the transition metal atom Pt(II) has a coordination number of 4, the number n of preferred monoanionic bidentate carbene ligands n is 1 or 2, preferably 1. In the case of n=2, the carbene ligands can be identical or different.

The process of the invention is very particularly preferably used for preparing a transition metal complex in which M$^1$ is Ir(III) having a coordination number of 6. In this Ir(III) complex, very particular preference is given to n being 3, m being 0, o being 0, q being 0, p being 0, Do$^1$ being N and r being 1, with the remaining symbols having the abovementioned meanings.

According to the invention, the cyclometallated carbene complexes of the formula I are obtained by reaction of a ligand precursor of the general formula (III)

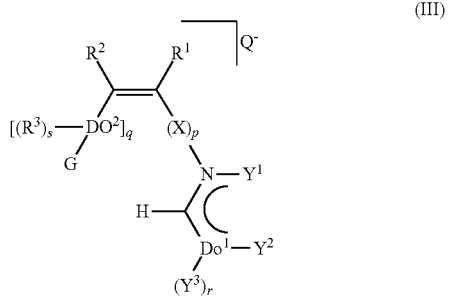

(III)

where
Q$^-$ is a monoanionic counterion, preferably halide, e.g. F$^-$, Cl$^-$, Br$^-$, I$^-$, pseudohalide, BF$_4^-$, BPh$_4^-$, PF$_6^-$, AsF$_6^-$ or SbF$_6^-$, particularly preferably halide, e.g. F$^-$, Cl$^-$, Br$^-$, I$^-$, or BF$_4^-$, very particularly preferably I$^-$ or BF$_4^-$; very particularly preferably I$^-$ or BF$_4^-$;
and
G is H when Do$^2$=C and
is H or a free electron pair when Do$^2$=N, S, O or P;
and
the further symbols in the ligand precursor of the formula III have the meanings given in respect of the ligand of the formula II,
wherein
the reaction comprises the use of a base and an auxiliary reagent selected from among salts of Ag, Hg, Sb, Mg, B and Al (route A) or the use of a basic auxiliary reagent comprising at least one metal selected from the group consisting of Ag, Hg, Sb, Mg, B and Al (route B) and the ligand precursor of the general formula III is
(A) reacted with the base, a metal complex comprising at least one metal M$^1$ and the auxiliary reagent (route A), or
(B) reacted with the basic auxiliary reagent to give a protected carbene and the protected carbene is subsequently reacted with a metal complex comprising at least one metal M$^1$ (route B).

The ligand precursors of the formula III are prepared by methods known to those skilled in the art. Suitable methods are mentioned, for example, in WO 2005/019373 and the literature cited therein, e.g. Organic Letters, 1999, 1, 953-956; Angewandte Chemie, 2000, 112, 1672-1674. Further suitable methods are mentioned, for example, in T. Weskamp et al., J. Organometal. Chem. 2000, 600, 12-22; G. Xu et al., Org. Lett. 2005, 7, 4605-4608; V. Lavallo et al., Angew. Chem. Int. Ed. 2005, 44, 5705-5709. Some of the suitable ligand precursors are commercially available.

In the process of the invention, the reaction of the ligand precursor of the formula III is carried out in the presence of a base and an auxiliary reagent (route A) or in the presence of a basic auxiliary reagent (route B). It has been found that cyclometallated metal complexes of the formula I can be obtained in good yields by means of the process of the invention.

In a preferred embodiment of the process of the invention, the metal complex comprising at least one metal M$^1$, the ligand precursor of the formula III, the base and the auxiliary reagent (route A) or the metal complex comprising at least one metal M$^1$, the ligand precursor of the formula III and the basic auxiliary reagent (route B) are used in particular ratios relative to one another.

In the case of route A of the process of the invention, the ratio of metal complex comprising at least one metal M$^1$, ligand precursor of the formula III, base and auxiliary reagent is preferably 1:1-10:1-10:0.5-15 per metal atom M$^1$ and number of carbene ligands n, particularly preferably 1:1-5:1-5:1-7, very particularly preferably 1:1-2: 1-2:1-1.5.

In the case of route B of the process of the invention, the ratio of metal complex comprising at least one metal M$^1$, ligand precursor of the formula III and basic auxiliary reagent is preferably 1:1-10:0.5-5 per metal atom M$^1$ and number of carbene ligands n, particularly preferably 1:1-5:0.5-2.5, very particularly preferably 1:1-3:0.5-1.5.

In general, the process of the invention is carried out in a solvent. Here, the term solvent encompasses both individual solvents and solvent mixtures. Preference is given to using aprotic solvents. The solvent is particularly preferably selected from at least one solvent selected from the group consisting of dioxane, butanone, THF, toluene, xylene, DMF, acetonitrile, DMSO, NMP and pyridine. Very particular preference is given to using a solvent which comprises dioxane as sole solvent or in admixture with one of the abovementioned solvents. It has surprisingly been found that particularly good yields can be achieved when the process of the invention is carried out in a solvent comprising dioxane.

The process of the invention is generally carried out at temperatures of from 60 to 200° C., preferably from 70 to 150° C.

The metal complex comprising at least one metal M$^1$ is a metal complex comprising at least one metal selected from the group consisting of Ir, Co, Rh, Ni, Pd, Pt, Fe, Ru, Os, Cr, Mo, W, Mn, Tc, Re, Cu and Au, preferably Ir, Os, Ru, Rh, Pd, Co and Pt, particularly preferably Ir, Pt, Rh and Os, very particularly preferably Ir, in any oxidation state possible for the respective metal atom, preferably Ir(I) or Ir(III), particularly preferably Ir(I). Suitable metal complexes are known to those skilled in the art. Examples of suitable metal complexes are Pt(cod)Cl$_2$, Pt(cod)Me$_2$, Pt(acac)$_2$, Pt(PPh$_3$)$_2$Cl$_2$, PtCl$_2$, [Rh(cod)Cl]$_2$, Rh(acac)CO(PPh$_3$), Rh(acac)(CO)$_2$, Rh(cod)$_2$BF$_4$, RhCl(PPh$_3$)$_3$, RhCl$_3$×nH$_2$O, Rh(acac)$_3$, [Os(CO)$_3$I$_2$]$_2$, [Os$_3$(CO)$_{12}$], OsH$_4$(PPH$_3$)$_3$, Cp$_2$Os, Cp*$_2$Os, H$_2$OsCl$_6$×6H$_2$O, OsCl$_3$×H$_2$O and also [(μ-Cl)Ir(η$^4$-1,5-cod)]$_2$, [(μ-Cl)Ir(η$^2$-coe)$_2$]$_2$, Ir(acac)$_3$, IrCl$_3$×nH$_2$O, (tht)$_3$IrCl$_3$, Ir(η$^3$-allyl)$_3$, Ir(η$^3$-methallyl)$_3$, where cod is cyclooctadiene, coe is cyclooctene, acac is acetylacetonate and tht is tetrahydrothiophene. The metal complexes can be prepared by methods known to those skilled in the art or are commercially available.

In the preparation of iridium(III) complexes of the general formula I (M$^1$ in formula I is Ir), which are particularly preferred according to the present patent application, it is possible to use, for example, iridium(I) or iridium(III) complexes, in particular [(µ-Cl)Ir($\eta^4$-1,5-cod)]$_2$, [(µ-Cl)Ir($\eta^2$-coe)$_2$]$_2$, Ir(acac)$_3$, IrCl$_3$×nH$_2$O, (tht)$_3$IrCl$_3$, Ir($\eta^3$-allyl)$_3$, Ir($\eta^3$-methallyl)$_3$, where cod is cyclooctadiene, coe is cyclooctene, acac is acetylacetonate and tht is tetrahydrothiophene. Particular preference is given to using Ir(I) complexes, very particularly preferably [(µ-Cl)Ir($\eta^4$-1,5-cod)]$_2$ or [(µ-Cl)Ir($\eta^2$-coe)$_2$]$_2$.

The auxiliary reagent used in the process of the invention according to route A and the basic auxiliary reagent used according to route B comprises a metal selected from the group consisting of Ag, Hg, Sb, Mg, B and Al, preferably Ag.

Route A

The process of the invention comprises, according to route A, the reaction of the ligand precursors of the general formula III with a base, a metal complex comprising at least one metal $M^1$ and an auxiliary reagent selected from among salts of Ag, Hg, Sb, Mg, B and Al.

Suitable ratios of metal complex comprising at least one metal $M^1$, ligand precursor of the formula III, base and auxiliary reagent, suitable solvents, suitable reaction temperatures and suitable metal complexes comprising at least one metal $M^1$ have been mentioned above.

Suitable auxiliary reagents used according to route A are selected from among salts of the abovementioned metals (Ag, Hg, Sb, Mg, B and Al, preferably Ag). Suitable salts are inorganic salts such as tetrafluoroborates, hexafluorophosphates, hexafluoroborates, hexafluoroantimonates, hexafluoroarsenates, thiocyanates, cyanates, nitrates, sulfates or perchlorates of the abovementioned metals or organic salts such as trifluoroacetates or triflates of the abovementioned metals. Here, the auxiliary reagents mentioned can be used individually or in the form of mixtures of two or more auxiliary reagents.

Preferred auxiliary reagents used in route A are Ag(I) salts. Suitable Ag(I) salts are, for example, selected from among inorganic salts such as AgBF$_4$, AgPF$_6$, AgSbF$_6$, AgAsF$_6$, AgSCN, AgOCN, AgNO$_3$, Ag$_2$SO$_4$, AgClO$_4$ and organic salts such as Ag(COOCF$_3$), Ag(OTf). Very particular preference is given to AgBF$_4$ and AgPF$_6$.

In route A of the process of the invention, preference is given to using a base selected from among alkali metal silylamides, alkali metal alkoxides, alkali metal hydrides, alkali metal acetates, alkali metal hydroxides, alkali metal carbonates, Grignard compounds, alkylmetal compounds and nitrogen-comprising bases as base. Here, the auxiliary reagents mentioned can be used individually or in the form of mixtures of two or more auxiliary reagents. Particular preference is given to using one or more bases selected from the group consisting of KHMDS, NaHMDS, LiHMDS, KO$^t$Bu, NaO$^t$Bu, LiO$^t$Bu, NaH, KOAc, NaOAc, LiOAc, NEt$_3$, BuLi, RMgHal, where R is alkyl, aryl, alkenyl, KOH, NaOH, LiOH, Cs$_2$CO$_3$, K$_2$CO$_3$, Na$_2$CO$_3$, Li$_2$CO$_3$, pyridine and DBU. Very particular preference is given to using KHMDS, NaHMDS and/or LiHMDS as base.

The reaction time in the case of route A is generally from 1 to 100 hours, preferably from 1 to 48 hours.

The reaction according to route A can be carried out in one or more stages.

The single-stage reaction is generally carried out by combining the ligand precursor of the general formula III, the base, the metal complex comprising at least one metal $M^1$ and the auxiliary reagent in a solvent and subsequently heating the mixture to the abovementioned reaction temperature. After the reaction time indicated above, the solvent is generally removed by methods known to those skilled in the art, usually under reduced pressure, and the residue which remains is worked up and/or purified by methods known to those skilled in the art. The work-up and purification are usually effected by extraction, column chromatography and/or recrystallization according to methods known to those skilled in the art.

In the case of a multistage reaction, all orders of addition known to those skilled in the art are possible. In a preferred embodiment, the multistage reaction is carried out according to the following steps:

(i) reaction of the ligand precursor of the formula III with the base to give a reaction mixture,
(ii) reaction of the metal complex comprising at least one metal $M^1$ with the auxiliary reagent to give a reaction mixture,
(iii) reaction of the reaction mixture obtained in step (i) with the reaction mixture obtained in step (ii)

to give a cyclometallated metal complex of the formula I.

The reaction is preferably carried out in one of the abovementioned solvents or solvent mixtures. Suitable ligand precursors of the general formula III, bases, metal complexes comprising at least one metal $M^1$ and auxiliary reagents have been mentioned above.

Step (iA)

The reaction in step (iA) is preferably carried out at room temperature in one of the abovementioned solvents or solvent mixtures. In general, the ligand precursor of the general formula III is admixed with the base and the reaction mixture obtained is stirred at room temperature.

Step (iiA)

The reaction in step (iiA) is generally likewise carried out at room temperature. In general, the metal complex comprising at least one metal $M^1$ and the auxiliary reagent are mixed in one of the abovementioned solvents or solvent mixtures and the mixture is stirred at room temperature.

Step (iiiA)

In step (iiiA) the reaction mixture obtained in step (iA) is added to the reaction mixture obtained in step (iiA). In principle, it is likewise possible to add the reaction mixture obtained in step (iiA) to the reaction mixture obtained in step (iA). In general, the addition is carried out at room temperature and the mixture is subsequently heated to the abovementioned reaction temperatures.

After the reaction time indicated above, the solvent is generally removed by methods known to those skilled in the art, preferably under reduced pressure. The reaction product is subsequently worked up and/or purified as mentioned above in respect of the single-stage process.

The respective reaction product obtained after the steps (iA) or (iiA) can be used directly without work-up or be worked up. In general, no work-up is carried out and the respective reaction product obtained is used directly in step (iiiA).

The desired cyclometallated carbene complexes of the formula I can be obtained in good yields and in high purity by means of the process of the invention according to route A comprising the use of a base and an auxiliary reagent.

The present invention further provides for the use of an auxiliary reagent selected from among salts comprising at least one metal selected from the group consisting of Ag, Hg, Sb, Mg, B and Al together with a base in a process for preparing cyclometallated carbene complexes.

Preferred auxiliary reagents and bases and also a preferred process for preparing the cyclometallated carbene complexes have been mentioned above.

Route B

According to route B, the process of the invention comprises reaction of the ligand precursors of the general formula III with the basic auxiliary reagent comprising at least one metal selected from the group consisting of Ag, Hg, Sb, Mg, B and Al to give a protected carbene and subsequent reaction of the protected carbene with a metal complex comprising at least one metal $M^1$.

Suitable ratios of metal complex comprising at least one metal $M^1$, ligand precursor of the formula III and basic auxiliary reagent, suitable solvents, suitable reaction temperatures and suitable metal complexes comprising at least one metal $M^1$ have been mentioned above.

The basic auxiliary reagents comprise the abovementioned metals (Ag, Hg, Sb, Mg, B and/or Al, preferably Ag). Suitable basic auxiliary reagents are the oxides, carbonates, acetates and/or sulfides of the abovementioned metals, preferably $Ag_2O$, $Ag_2CO_3$, AgOAc and/or $Ag_2S$. In a further preferred embodiment, the oxides of the abovementioned metals are used, with particular preference being given to silver(I) oxide, $Ag_2O$.

The reaction time according to route B is generally from 1 to 100 hours, preferably 6 to 56 hours.

The reaction according to route B of the process of the invention is carried out as a multistage reaction according to the following steps:
(iB) reaction of the ligand precursor of the general formula III with the basic auxiliary reagent comprising at least one metal selected from the group consisting of Ag, Hg, Sb, Mg, B and Al to give a metal-carbene complex,
(iiB) subsequent reaction of the metal-carbene complex with a metal complex comprising at least one metal $M^1$
to give a cyclometallated metal complex of the formula I.

The reaction is preferably carried out in one of the abovementioned solvents or solvent mixtures. Suitable ligand precursors of the general formula III, metal complexes comprising at least one metal $M^1$ and basic auxiliary reagents have been mentioned above.

Step (iB)

The reaction in step (iB) is preferably carried out at room temperature in one of the abovementioned solvents or solvent mixtures. A metal-carbene complex is obtained.

Step (iiB)

In step (iiB), the metal-carbene complex obtained in step (iB) is reacted with the metal complex comprising at least one metal $M^1$. In a preferred embodiment, the metal complex comprising at least one metal $M^1$ is added to the metal-carbene complex obtained in step (iB). The reaction mixture is stirred at the temperatures indicated above.

After the reaction time indicated above, the precipitate usually formed is generally filtered off and washed with the solvent or solvent mixture which is preferably used. The filtrate obtained is generally evaporated to dryness by methods known to those skilled in the art, usually by removal of the solvent under reduced pressure. The reaction product obtained is generally worked up and/or purified further.

The work-up and purification are usually effected by extraction, column chromatography and/or recrystallization according to methods known to those skilled in the art.

The metal-carbene complex obtained in step (iB) can be used directly without work-up or be worked up. In general, the metal-carbene complex obtained is used without further work-up and/or purification in the subsequent step (iiB).

The desired cyclometallated carbene complexes of the formula I can be obtained in good yields and in high purity by means of the two-stage process of the invention according to route B comprising the use of a basic auxiliary reagent.

If the process of the invention according to route A or B is used for preparing cyclometallated carbene complexes of the formula I which can form cis/trans isomers or fac/mer isomers (facial/meridional isomers), the process of the invention generally gives a mixture of the cis and trans isomers or fac and mer isomers (facial/meridional isomers). These isomer mixtures can be separated by methods known to those skilled in the art, so that the pure cis or trans isomers or fac or mer isomers are obtainable in each case.

The following examples illustrate the invention.

EXAMPLES

Method A for the Synthesis of the Complex

Potassium bis(trimethylsilyl)amide (0.5 M in toluene; 5 eq) is added to a suspension of (benz)imidazolium salt (5 eq) in dioxane under argon over a period of 30 minutes. The mixture is stirred at room temperature for one hour before being added to a suspension of 1,5-cyclooctadieneiridium(I) chloride dimer (0.5 eq) and $AgBF_4$ (1 eq) in dioxane under argon over a period of 30 minutes. The reaction mixture is subsequently stirred at room temperature for one hour, at 70° C. for two hours and under reflux for 22 hours.

Method B for the Synthesis of the Complex

A suspension of (benz)imidazolium salt (5 eq) and silver(I) oxide (2.5 eq) in dioxane is stirred at room temperature under argon for 16 hours. The mixture is admixed with 1,5-cyclooctadieneiridium(I) chloride dimer (0.5 eq) and stirred under reflux for 16 hours. After cooling to room temperature, the precipitate is filtered off and washed with dioxane. The combined filtrates are evaporated to dryness and the crude product is purified by column chromatography on basic aluminum oxide.

Example 1

Synthesis of Ir(cn-pmic)$_3$

Synthesis of 1-(4-cyanophenyl)imidazole 1500 ml of dry dimethylformamide (DMF) are placed in a 1000 ml four-necked flask while passing nitrogen over it and 72.67 g (0.6 mol) of 4-fluorocyanobenzene and 61.2 g (0.9 mol) of imidazole and finally 21.6 g (0.9 mol) of sodium hydride are added. The reaction mixture is heated to 100° C., stirred at this temperature for 4 hours and subsequently overnight at room temperature. The reaction mixture is then poured into water and the resulting mixture is extracted a number of times with dichloromethane. The organic phase is dried, evaporated on a rotary evaporator and finally dried further at 60° C. under reduced pressure. The yield is 94 g (93% of theory).
$^1$H-NMR (400 MHz, CDCl$_3$): δ=7.27 (s, 1H); 7.35 (s, 1H); 7.54 (d, J=8.8 Hz, 2H); 7.81 (d, J=8.8 Hz, 2H); 7.95 (s, 1H).

Synthesis of
1-(4-cyanophenyl)-3-methylimidazolium iodide 56 g (0.33 mol) of 1-(4-cyanophenyl)imidazole are dissolved in 560 ml water-free tetrahydrofuran in a 2000 ml one-necked flask with condenser, admixed with 234.2 g (1.65 mol) of methyl iodide, stirred briefly and allowed to stand for 48 hours without further stirring. The solid contents of the flask are subsequently slurried with ethanol, filtered off with suction and washed with ethanol until the washings are virtually colorless. The residue is dried at 70° C. under reduced pressure. The yield is 81.54 g (80% of theory).

$^1$H-NMR (400 MHz, DMSO): δ=3.97 (s, 3H); 8.00-8.04 (m, 3H); 8.22 (d, J=9.0 Hz, 2H); 8.40 (dd, J=1.8, 1.8 Hz, 1H); 9.91 (s, 1H). Elemental analysis: calculated for $C_{11}H_{10}IN_3$: C, 42.4; H, 3.3; N, 13.5; I, 40.0. found: C, 42.6; H, 2.9; N, 13.6; I, 40.9.

Synthesis of mer-tris[1-(4'-cyanophenyl)-3-methylimidazol-2-ylidene-$C^2,C^{2'}$]iridium(III)

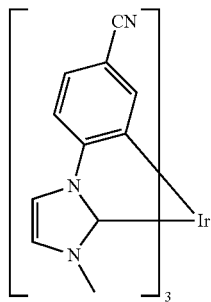

Synthesis Procedure 1:

The product is prepared by method A. The solvent is removed under reduced pressure and the residue which remains is extracted with methylene chloride. Purification of the extract by column chromatography gives the product as a yellowish powder (58% of theory).

Synthesis Procedure 2:

The product is prepared by method B and eluted with dichloromethane. The isomer mixture obtained is separated by column chromatography in silica gel using ethyl acetate/cyclohexane 9:1 or by fractional precipitation from acetonitrile. Yield: 75% mer isomer and 4% fac isomer.

Comparative Example 1

Synthesis Procedure 3 (Like Method B without Ag Salt)

10 g (32 mmol) of the imidazolium iodide together with 150 ml of dioxane are placed in a 500 ml three-necked flask and 64.3 ml of potassium bis(trimethylsilyl)amide (0.5 M in toluene, 32 mmol) are added at room temperature over a period of 30 minutes. The mixture is stirred at room temperature for one hour before being added to a suspension of 2.16 g (3.2 mmol) of 1,5-cyclooctadieneiridium(I) chloride dimer in 200 ml of dioxane under argon over a period of 30 minutes. The reaction mixture is stirred at room temperature for one hour, at 70° C. for two hours and under reflux for 22 hours. The mixture is subsequently evaporated to dryness and the residue is extracted with methylene chloride. Purification of the extract by column chromatography gives the product as a yellowish powder (24% of theory).

The yield of the desired product is significantly lower in Comparative Example 1 than in Example 1 (synthesis procedures 1 and 2) according to the process of the invention.

$^1$H-NMR (CD$_2$Cl$_2$, 400 MHz): δ=2.97 (s, 3H), 3.05 (s, 6H), 6.77 (d, J 2.0, 1H), 6.85 (d, J 2.5, 1H), 6.88 (d, J 2.5, 1H), 6.89 (d, J 2.0, 1H), 6.98-7.00 (m, 1H), 7.04-7.05 (m, 1H), 7.21-7.30 (m, 6H), 7.46 (d, J 2.0, 1H), 7.52 (d, J 2.0, 1H), 7.53 (d, J 2.0, 1H).

Example 2

Synthesis of Ir(cn-pmbic)$_3$

Synthesis of 1-(4-cyanophenyl)benzimidazole (K. Nishiura, Y. Urawa, S. Soda, *Adv. Synth. Catal.* 2004, 346, 1679)

Sodium hydride (60% strength in mineral oil; 24.0 g, 0.60 mol) is placed in a flask and admixed with N,N-dimethylformamide (80 ml). A solution of benzimidazole (73.3 g, 0.60 mol) in N,N-dimethylformamide (250 ml) is added dropwise to the suspension over a period of 1 hour. After H$_2$ evolution has ceased 4-chlorobenzonitrile (55.6 g, 0.40 mol) is added and the mixture is subsequently heated at 130° C. for 10.5 hours. After cooling to room temperature, the reaction mixture is poured into water (4 l) and the residue formed is filtered off with suction, washed with water and dried under reduced pressure. This gives 90.6 g of 1-(4-cyanophenyl)benzimidazole which still comprises mineral oil as contaminant.

$^1$H-NMR (400 MHz, CD$_2$Cl$_2$): δ=7.35-7.41 (m, 2H), 7.59-7.63 (m, 1H), 7.70 (d, J=8.5 Hz, 2H), 7.83-7.86 (m, 1H), 7.90 (d, J=8.5 Hz, 2H), 8.15 (s, 1H).

Synthesis of 1-(4-cyanophenyl)-3-methylbenzimidazolium iodide 1-(4-Cyanophenyl)benzimidazole (90 g, slightly contaminated with mineral oil) together with THF (250 ml) is placed in a reaction vessel, admixed with methyl iodide (116 g, 0.82 mol) and maintained at 40° C. for 25.5 hours. The residue formed is filtered off, washed with ethanol and dried under reduced pressure. This gives 123 g of 1-(4-cyanophenyl)-3-methylbenzimidazolium iodide.

$^1$H-NMR (400 MHz, DMSO): δ=4.20 (s, 3H), 7.74-7.84 (m, 2H), 7.93 (d, J=8.4 Hz, 1H), 8.07 (d, J=8.8 Hz, 2H), 8.18 (d, J=8.4 Hz, 1H), 8.30 (d, J=8.8 Hz, 2H), 10.24 (s, 1H).

Synthesis of mer-tris[1-(4'-cyanophenyl)-3-methylbenzimidazol-2-ylidene-$C^2,C^{2'}$]iridium(III)

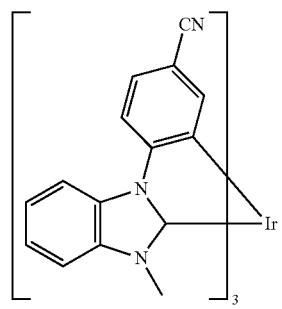

Synthesis Procedure 1:

The product is prepared by method A. The solvent is removed under reduced pressure and the residue which remains is extracted with methylene chloride. Purification of the extract by column chromatography gives the product as a yellowish powder (60% of theory).

Synthesis Procedure 2:

The product is prepared by method B and eluted with ethyl acetate/methanol 2:1. Yield: 65%.

$^1$H-NMR (d$_6$-DMSO, 500 MHz): δ=3.18 (s, 3H), 3.22 (s, 3H), 3.29 (s, 3H), 6.81 (d, J 2.0, 1H), 7.03 (d, J 2.0, 1H), 7.10

(d, J 2.0, 1H), 7.30-7.47 (m, 12H), 7.94 (d, J 8.0, 1H), 7.95 (d, J 3.5, 1H), 7.97 (d, J 3.5, 1H), 8.15 (d, J 8.0, 1H), 8.16 (d, J 3.5, 1H), 8.17 (d, J 3.5, 1H). $^{13}$C-NMR (CD$_2$Cl$_2$, 125 MHz): δ=187.0, 185.0, 183.7 (NCN), 153.4, 152.6, 151.8, 150.5, 149.7, 147.5 (Cq or CN), 141.9, 141.7, 139.9 (CH$_{Ph}$), 137.10, 137.07, 136.7, 132.63 (2), 132.59 (Cq or CN), 127.1, 127.0, 126.7, 124.3, 124.2 (2), 123.71, 123.66, 123.5, (CH$_{Ph}$), 120.68, 120.66, 120.65 (Cq or CN), 113.1, 112.9, 112.5, 112.2, 112.1, 111.9, 111.1, 110.9 (2) (CH$_{Ph}$), 108.6, 108.3, 108.2 (Cq or CN), 34.3, 34.2, 33.5 (NCH$_3$). Thermogravimetric analysis/differential thermal analysis (heating rate: 5 K/min): loss of solvent above about 30° C.; commencement of decomposition about 410° C. HPLC: >99.8% by area (column: Purospher Star Si 5 μm, eluent: heptane/i-propanol=65/35 (% by volume)).

Example 3

Synthesis of Ir(pmic)$_3$

Synthesis of mer-tris[1-phenyl-3-methylimidazol-2-ylidene-C$^2$,C$^{2'}$]iridium(III)

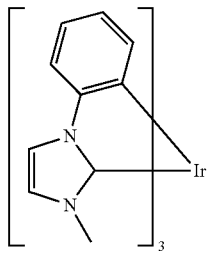

For ligand synthesis, see WO 2005/113704.
Synthesis Procedure 1 (Two-Stage Process, Route B)
The product is prepared by method B and eluted with ethyl acetate/cyclohexane 1:1.
Yield: 64%.
$^1$H-NMR (CD$_2$Cl$_2$, 400 MHz): δ=2.96 (s, 3H), 3.04 (s, 3H), 3.05 (s, 3H), 6.55-6.67 (m, 4H), 6.73-6.88 (m, 8H), 7.09-7.14 (m, 3H), 7.36 (d, J 2.0, 1H), 7.42 (d, J 2.0, 1H), 7.46 (d, J 2.0, 1H).

Comparative Example 3

Synthesis Procedure 2 (Using Ag$_2$O in a One-Pot Process)

(T. Sajoto et al., Inorg. Chem. 2005, 44, 7992-8003)
A 50 ml round-bottomed flask is charged with silver(I) oxide (0.076 g, 0.328 mol), 1-phenyl-3-methylimidazolium iodide (0.109 g, 0.381 mmol), iridium trichloride hydrate (0.029 g, 0.097 mmol) and 20 ml of 2-ethoxyethanol. The reaction mixture is stirred and heated at 120° C. under nitrogen on an oil bath for 15 hours with the reaction mixture being protected from light by means of aluminum foil. The reaction mixture is cooled to room temperature and evaporated under reduced pressure. To remove the silver(I) salts, the mixture is filtered through Celite using dichloroethane as eluent. Removal of the solvent under reduced pressure gives a white solid which is washed with methanol. This gives 0.016 g (24% yield) of the meridional trisiridium complex in the form of a white solid.

The yield of the desired product is significantly lower in Comparative Example 3 than in Example 3 according to the process of the invention.

Example 4

Synthesis of Ir(cl-pmic)$_3$

Synthesis of 1-(4-chlorophenyl)imidazole (S. U. Son, I. K. Park, J. Park, T. Hyeon, Chem. Commun. 2004, 778)
1-Chloro-4-fluorobenzene (16.3 g, 124 mmol) and imidazole (5.0 g, 73.4 mmol) are dissolved in N,N-dimethylformamide (30 ml) and admixed while stirring with sodium hydride (60% strength in mineral oil; 3.82 g, 95.4 mmol) and then heated at 130° C. for 5 hours. After cooling, the reaction mixture is slowly poured into water. The precipitate formed is subsequently filtered off, washed with petroleum ether and subsequently dried under reduced pressure. This gives 10.3 g of 1-(4-chlorophenyl)imidazole.
$^1$H-NMR: (400 MHz, CD$_2$Cl$_2$): δ=7.16 (brs, 1H), 7.30 (dd, J=1.2, 1.2 Hz, 1H), 7.38 (d, J=7.7 Hz, 2H), 7.48 (d, J=7.7 Hz, 2H), 7.82 (brs, 1H).

Synthesis of 1-(4-chlorophenyl)-3-methylimidazolium iodide 1-(4-Chlorophenyl)imidazole (0.37 g, 2.07 mmol) is dissolved in THF (5 ml) and subsequently admixed with methyl iodide (1.47 g, 10.4 mmol) and allowed to stand for 20 hours. The precipitate formed is subsequently filtered off and washed with ethanol and with petroleum ether and subsequently dried under reduced pressure. This gives 0.46 g of 1-(4-chlorophenyl)-3-methylimidazolium iodide.
$^1$H-NMR (400 MHz, DMSO): δ=3.96 (s, 3H), 7.76-7.84 (m, 4H), 7.97 (dd, J=1.8, 1.8 Hz, 1H), 8.30 (dd, J=1.8, 1.8 Hz, 1H), 9.80 (brs, 1H).

Synthesis of mer-tris[1-(4'-chlorophenyl)-3-methylimidazol-2-ylidene-C$^2$,C$^{2'}$]iridium(III)

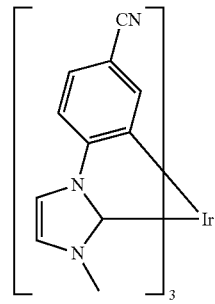

The product is prepared by method A. After cooling, the precipitate is filtered off and the filtrate is subjected to purification by column chromatography. This gives the product as a white powder (79% of theory).
$^1$H-NMR: (CD$_2$Cl$_2$, 500 MHz): δ=7.43 (m, 2H), 7.38 (m, 1H), 7.08 (m, 3H), 6.90-6.75 (m, 6H), 6.67 (m, 2H), 6.42 (m, 1H) (each CH$_{Ph}$ or NCHCHN), 3.06 (s, 3H, NCH$_3$), 3.02 (s, 3H, NCH$_3$), 2.99 (s, 3H, NCH$_3$). $^{13}$C-NMR (CD$_2$Cl$_2$, 125 MHz): δ=173.9, 172.1, 171.3 (NCN), 153.9, 152.7, 151.2, 147.1, 146.4, 145.7 (Cq), 138.5, 138.1, 136.6 (CH$_{Ph}$ or NCHCHN), 130.5, 130.3, 130.2 (Cq), 121.8, 121.6, 121.3, 120.5, 120.3, 120.1, 115.04, 114.99, 114.9, 112.00, 111.97, 111.5 (CH$_{Ph}$ or NCHCHN), 37.4 (double intensity), 36.2 (NCH$_3$).

Example 5

Synthesis of Ir(pymic)$_3$

Synthesis of 1-(4'-pyridyl)-3-methylimidazolium chloride

4-Chloropyridine hydrochloride (91.6 g, 0.61 mol) is admixed with saturated sodium hydrogencarbonate solution and extracted four times with dichloromethane. The combined organic phases are dried over sodium sulfate, filtered and evaporated to dryness. The oil obtained (52.7 g, 0.46 mol) is admixed with methylimidazole (38.1 g, 0.46 mol) and stirred at 130° C. for 6 hours. After cooling to room temperature, the mixture is dissolved in ethanol and the product is precipitated by addition of n-hexane.

Yield: 56.7 g (0.29 mol, 63%).

$^1$H-NMR (d$_6$-DMSO, 400 MHz): δ=4.00 (s, 3H), 7.98 (dd, J 4.5, 1.5, 2H), 8.07 (m, 1H), 8.58 (m, 1H), 8.86 (dd, J 4.5, 1.5, 2H), 10.42 (s, 1H).

Synthesis of mer-tris[1-(4'-pyridyl)-3-methylimidazol-2-ylidene-C$^2$,C$^{2'}$]iridium(III)

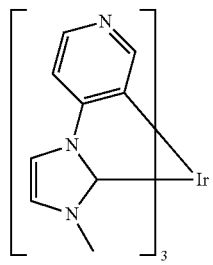

The product is prepared by method B in pyridine as solvent and eluted by means of isobutanol. Yield: 46%.

$^1$H-NMR (CD$_2$Cl$_2$, 400 MHz): δ=3.03 (s, 3H), 3.07 (s, 3H), 3.10 (s, 3H), 6.82-6.86 (m, 3H), 7.02-7.06 (m, 3H), 7.45 (d, J 2.0, 1H), 7.51 (d, J 2.0, 1H), 7.54 (d, J 2.0, 1H), 7.66 (d, J 0.5, 1H), 7.80 (d, J 0.5, 1H), 7.89 (d, J 0.5, 1H), 8.04 (d, J 5.0, 1H), 8.07 (d, J 5.0, 1H), 8.08 (d, J 5.0, 1H). ESI-MS (MeCN/H$_2$O 8:2): m/e=666.1844 (M+H$^+$, correct isotope pattern, calc.: 666.1839).

Example 6

Synthesis of Ir(pombic)$_3$

Synthesis of 2-[(2,6-dinitrophenyl)amino]phenol

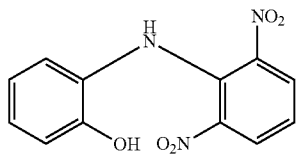 [SMILES: O=[N+]([O-])c1cccc([N+](=O)[O-])c1Nc1ccccc1O]

The preparation is carried out by the method of F. Ullmann, G. Engi, N. Wosnessenky, E. Kuhn and E. Herre, Liebigs Ann. 365 (1909) 79, 110.

17.30 g (157 mmol) of 99% strength 2-aminophenol and 17.15 g (209 mmol) of anhydrous sodium acetate are added to a solution of 25.0 g (121 mmol) of 98% strength 2,6-dinitrochlorobenzene in 185 ml of anhydrous ethanol under nitrogen while stirring. The reaction solution is refluxed for 2 hours and subsequently cooled to room temperature. The red-violet crystalline needles are separated off on a "black band" filter, washed with water until the washings are colorless and dried at 50° C. under reduced pressure. This gives 27.90 g (84% of theory) of shiny black needles which melt at 189-192° C. (lit.: 191° C.).

Synthesis of 4-nitrophenoxazine

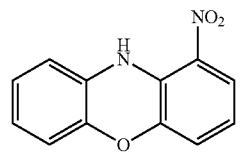 [SMILES: O=[N+]([O-])c1cccc2c1Nc1ccccc1O2]

The preparation is carried out by the method of F. Ullmann, G. Engi, N. Wosnessenky, E. Kuhn and E. Herre, Liebigs Ann. 365 (1909) 79, 110.

27.70 g (101 mmol) of 2-[(2,6-dinitrophenyl)amino]phenol are refluxed in 666 ml of 1% strength NaOH for 30 minutes while stirring. After cooling to room temperature, the solid is filtered off with suction, washed with hot water until neutral and dried at 80° C. under reduced pressure. This gives 21.2 g (92% of theory) of black crystals which melt at 168-171° C. (lit.: 166° C.).

Synthesis of 1-ammoniophenoxazine chloride

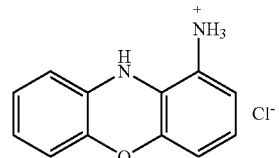

The preparation is carried out by the method of F. Kehrmann and L. Löwy, Ber. dtsch. chem. Ges. 44 (1911) 3006-3011.

21.20 g (92.9 mmol) of 1-nitrophenoxazine are suspended in 177 ml of anhydrous ethanol and admixed with a solution of 83.84 g (372 mmol) of tin(II) chloride×2H$_2$O in 101 ml of concentrated HCl. The reaction mixture is refluxed for 1 hour. After the reaction mixture has been cooled to room temperature, the precipitate is filtered off with suction, washed four times with a total of 430 ml of 10% strength HCl, then with cold water and dried at 70° C. under reduced pressure. This gives 18.45 g of gray needles.

Synthesis of 2,10b-diaza-6-oxaaceanthrylene(imidazo[4,5,1-k,l]phenoxazine)

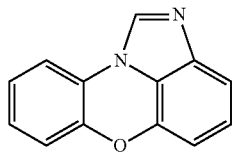 [SMILES: c1ccc2c(c1)Oc1cccc3ncn-2c13]

The preparation is carried out by a method based on those of H. Shirai and T. Hayazaki, Yakugaku Zasshi 90 (1970) 588-593 and A. N. Gritsenko, Z. I. Ermakova, V. S. Troitskaya and S. V. Zhuravlev, Chem. Heterocycl. Compd. 1971, 715-717.

18.45 g (78.6 mmol) of 1-ammoniophenoxazine chloride are suspended in 85 ml of 85% strength formic acid. After addition of 5.38 g (78.6 mmol) of sodium formate, the reaction mixture is refluxed for 3.5 hours. After cooling to room temperature, the reaction mixture is precipitated in 700 g of 10% strength NaOH and stirred for another 30 minutes. The solid is filtered off with suction on a "black band" filter, washed with water and dried at 70° C. under reduced pressure. The crude product (16.35 g) is stirred in 160 ml of methanol for 2 hours, subsequently filtered off with suction, washed with methanol and dried at 70° C. This gives 13.09 g (80% of theory) of gray needles which melt at 177-181° C. (lit.: 177-178° C.).

Synthesis of 10b-aza-2-azonia-2-methyl-6-oxaaceanthrylene iodide (2-methylimidazo[4,5,1-k,l]phenoxazonium iodide)

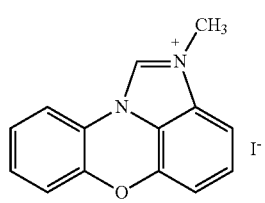

The preparation is carried out by a method based on that of H. Shirai and T. Hayazaki, Yakugaku Zasshi 90 (1970) 588-593.

A solution of 5.48 g (26.3 mmol) of 2,10b-diaza-6-oxaaceanthrylene and 18.42 g (130 mmol) of methyl iodide in 75 ml of methylene chloride are refluxed for 26 hours. After the reaction mixture has been cooled to room temperature, the solid is filtered off with suction, washed with methylene chloride and dried at 75° C. under reduced pressure. This gives 8.35 g (91% of theory) of analytically pure gray microcrystals which melt at 284-291° C. (lit.: 295-297° C.).

Synthesis of 10b-aza-2-azonia-2-methyl-6-oxaaceanthrylene tetrafluoroborate (2-methylimidazo[4,5,1-k,l]phenoxazonium tetrafluoroborate)

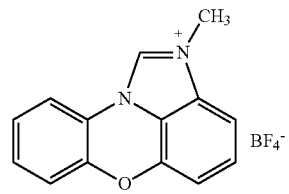

7.55 g (50.0 mmol) of 98% strength trimethyloxonium tetrafluoroborate are added to a solution of 10.41 g (50.0 mmol) of 2,10b-diaza-6-oxaaceanthrylene in 620 ml of water-free methylene chloride which has been cooled to 0-3° C. in an ice bath. The reaction mixture is allowed to warm to room temperature and stirred overnight. Another 0.755 g (5.0 mmol) of 98% strength trimethyloxonium tetrafluoroborate is added. After stirring at room temperature for 4 hours, the precipitate is filtered off with suction, washed with methylene chloride and dried at 40° C. under reduced pressure (crude yield: 11.35 g). The solid is recrystallized from 1000 ml of methanol under nitrogen. This gives 8.90 g of analytically pure dark gray microcrystals having a melting point of 230-238° C. The filtrate is evaporated to dryness. The solid (3.39 g) is recrystallized from 132 ml of methanol. This gives another 1.42 g of dark gray microcrystals, so that the total is 10.32 g (67% of theory).

$^1$H-NMR (500 MHz, DMSO): δ=4.10 (s, 3H), 7.18 (d, 1H), 7.37-7.61 (m, 5H), 7.93 (d, 1H), 10.25 (s, 1H).

Synthesis of mer-Ir(pombic)$_3$

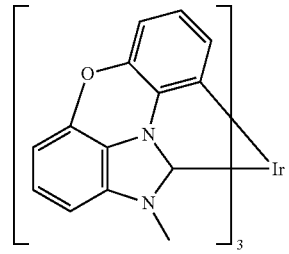

The product is prepared by method A in o-xylene as solvent. After cooling, the precipitate is filtered off and the filtrate is subjected to purification by column chromatography. This gives the product as a yellowish powder (21% of theory).

$^1$H-NMR: (CD$_2$Cl$_2$, 500 MHz): δ=6.99 (m, 3H, CH$_{Ph}$), 6.78 (m, 3H, CH$_{Ph}$), 6.63 (m, 8H, CH$_{Ph}$), 6.52 (m, 3H, CH$_{Ph}$), 6.41 (m, 1H, CH$_{Ph}$), 3.47 (s, 3H, CH$_3$), 3.45 (s, 3H, CH$_3$), 3.33 (s, 3H, CH$_3$). $^{13}$C-NMR (CD$_2$Cl$_2$, 125 MHz): δ=170.18, 168.16, 166.87 (NCN), 145.08, 144.61, 144.42, 144.34, 144.01, 143.49, 143.45, 143.44, 142.31, 136.29 (C$_q$), 136.25 (CH$_{Ph}$), 136.18, 135.98 (C$_q$), 135.79, 133.76 (CH$_{Ph}$), 131.92, 131.24, 130.51 (C$_q$), 126.61, 126.48, 126.43, 125.51, 125.34, 125.28 (CH$_{Ph}$), 124.03, 124.01, 123.92 (C$_q$), 109.86, 109.79, 109.47, 106.46, 106.32, 106.27, 105.50, 105.49, 105.46 (CH$_{Ph}$), 33.98, 33.64, 33.55 (CH$_3$).

Example 7

Synthesis of Pt(cn-pmic)(acac)

Synthesis of 1-(2-bromo-4-cyanophenyl)imidazole

3-Bromo-4-fluorobenzonitrile (10.0 g, 50 mmol, 1 eq) and imidazole (5.1 g, 75 mmol, 1.5 eq) are dissolved in dimethylformamide (100 ml) and carefully admixed with sodium hydride (60% in mineral oil, 3.0 g, 75 mmol, 1.5 eq) under nitrogen at room temperature. The mixture is stirred at 100° C. for 4 hours. After cooling to room temperature, water (10 ml) is added and the mixture is evaporated to dryness. The residue is washed with water and petroleum ether and purified by column chromatography (silica gel, methyl tert-butyl ether/ethyl acetate gradient).

Yield: 5.4 g (22 mmol, 44%).
$^1$H-NMR (CD$_2$Cl$_2$, 400 MHz): δ=7.15 (m$_c$, 1H), 7.52 (m$_c$, 1H), 7.74 (d, J 8.0, 1H), 7.99 (m$_c$, 1H), 8.06 (dd, J 8.0, 2.0, 1H), 8.48 (d, J 2.0, 1H).

Synthesis of 1-(2-bromo-4-cyanophenyl)-3-methylimidazolium iodide 1-(2-Bromo-4-cyanophenyl)imidazole (5.4 g, 22 mmol, 1 eq) and methyl iodide (15.4 g, 109.0 mmol, 5 eq) are dissolved in tetrahydrofuran (50 ml) and stirred at room temperature for 16 hours. The precipitate formed is filtered off and washed with ethanol.

Yield: 6.7 g (17 mmol, 78%).
$^1$H-NMR (d$_6$-DMSO/CD$_2$Cl$_2$ 1:1, 400 MHz): δ=4.17 (s, 3H), 7.77 (t, J 2.0, 1H), 7.90 (t, J 2.0, 1H), 7.96 (dd, J 8.0, 2.0, 1H), 8.16 (d, J 8.0, 1H), 8.20 (d, J 2.0, 1H), 9.96 (s, 1H).

Synthesis of [1-(4'-cyanophenyl)-3-methylimidazol-2-ylidene-C$^2$,C$^{2'}$]platinum(II) acetylacetonate

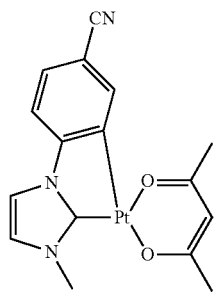

A suspension of 1-(2-bromo-4-cyanophenyl)-3-methylimidazolium iodide (0.62 g, 1.6 mmol, 1 eq) and silver(I) oxide (0.19 g, 0.8 mmol, 0.5 eq) in dioxane (80 ml) is stirred under argon at room temperature for 16 hours. The mixture is admixed with butanone (40 ml) and 1,5-cyclooctadieneplatinum(II) dichloride (0.60 g, 1.6 mmol, 1 eq) and stirred under reflux for 16 hours. After cooling to room temperature, the mixture is evaporated to dryness. The residue is taken up in dimethylformamide (80 ml) and admixed with 2,4-pentanedione (0.65 g, 6.4 mmol, 4 eq) and potassium tert-butoxide (0.73 g, 6.4 mmol, 4 eq). The mixture is stirred at room temperature for 16 hours and at 100° C. for 6 hours. After cooling to room temperature, it is evaporated to dryness and the residue is washed with water.

Yield: 0.53 g (1.1 mmol, 70%).
$^1$H-NMR (d$_6$-DMSO, 400 MHz): δ=1.97 (s, 3H), 2.04 (s, 3H), 4.01 (s, 3H), 5.64 (s, 1H), 7.45 (d, J 2.0, 1H), 7.48 (s, 1H), 7.51 (d, J 1.5, 1H), 7.78 (d, J 1.5, 1H), 8.06 (d, J 2.0, 1H). Cl-MS (MeCN/H$_2$O 8:2): m/e=476 (M+H$^+$, correct isotope pattern).

Example 8

Synthesis of Rh(cn-pmic)$_3$

Synthesis of mer-tris[1-(4'-cyanophenyl)-3-methylimidazol-2-ylidene-C$^2$,C$^{2'}$]rhodium(III)

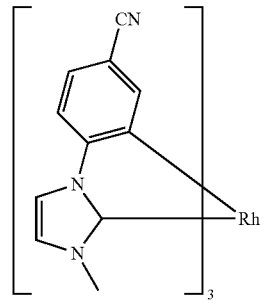

The product is prepared by method A using 1,5-cyclooctadienerhodium(I) chloride dimer. The solvent is removed under reduced pressure and the residue which remains is extracted with methylene chloride. Purification of the extract by column chromatography gives the product as a light-yellow powder (21% of theory).

$^1$H-NMR: (CD$_2$Cl$_2$, 500 MHz): δ=7.56 (d, J=1.9 Hz, 1H), 7.55 (d, J=2.0 Hz, 1H), 7.49 (d, J=1.9 Hz, 1H), 7.27-7.11 (m, 6H), 6.97, 6.93 (each s, 1H), 6.89 (d, J=1.8 Hz, 1H), 6.86 (d, J=1.7 Hz, 2H), 6.71 (s, 1H), 3.03 (s, 6H, CH$_3$), 2.96 (s, 3H, CH$_3$). $^{13}$C-NMR (CD$_2$Cl$_2$, 125 MHz): δ=190.3 (d, $^1$J$_{C,Rh}$=38.4 Hz, NCN), 189.5 (d, $^1$J$_{C,Rh}$=38.1 Hz, NCN), 188.2 (d, $^1$J$_{C,Rh}$=38.3 Hz, NCN), 166.7 (d, $^1$J$_{C,Rh}$=27.5 Hz, C$_q$), 166.0 (d, $^1$J$_{C,Rh}$=24.5 Hz, C$_q$), 164.5 (d, $^1$J$_{C,Rh}$=24.4 Hz, C$_q$), 150.5, 150.0, 149.3 (Cq), 142.4, 142.2, 140.4, 126.5, 126.4, 126.3, 123.0, 122.8, 122.5, 114.72, 114.68, 114.6, 110.9, 110.7, 110.4 (CH$_{Ph}$, NCHCHN), 120.9 (double intensity, C$_q$), 120.8 (C$_q$), 107.6 (d, J=1.8 Hz, C$_q$), 107.2 (d, J=1.9 Hz, C$_q$), 107.2 (d, J=1.6 Hz, C$_q$), 37.3, 37.2, 36.1 (CH$_3$).

The invention claimed is:
1. A process for preparing a cyclometallated carbene complex of the general formula (1) comprising at least one carbene ligand

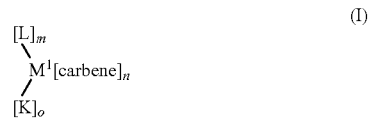

(I)

where the symbols have the following meanings:
M$^1$ is a metal atom selected from the group consisting of Ir, Co, Rh, Ni, Pd, Pt, Fe, Ru, Os, Cr, Mo, W, Mn, Tc, Re, Cu and Au in any oxidation state possible for the respective metal atom;

carbene is a carbene ligand
selected from the group consisting of carbene ligands a-j:
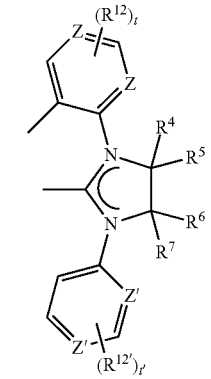  a
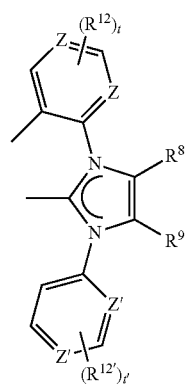  b
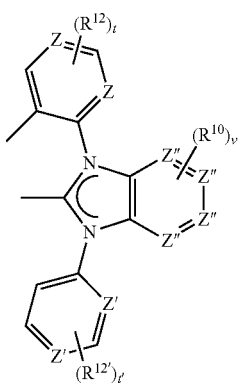  c
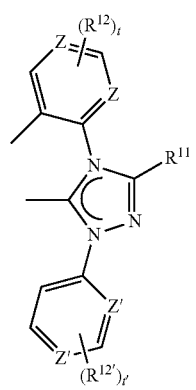  d
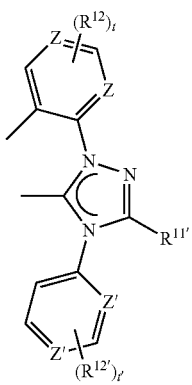  e
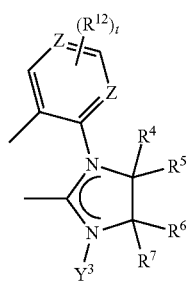  f
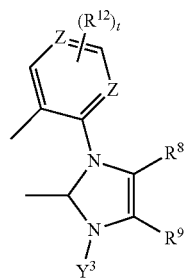  g
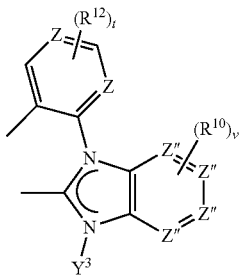  h
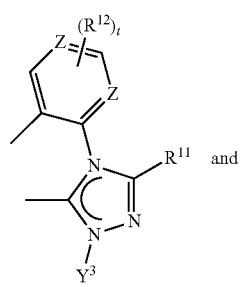  i and j

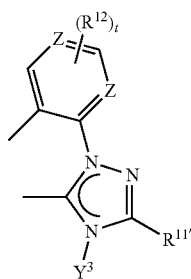

where the symbols have the following meanings:

Z, Z', Z" are identical or different and are each CH or N;

$R^{12}$, $R^{12'}$ are identical or different and are each an alkyl, aryl, heteroaryl, alkynyl or alkenyl radical, or 2 radicals $R^{12}$ or $R^{12'}$ together form a fused-on ring which may optionally comprise at least one heteroatom, or $R^{12}$ or $R^{12'}$ is a radical having a donor or acceptor action;

t and t' are identical or different and are each from 0 to 4, where, when t or t' is >1, the radicals $R^{12}$ or $R^{12'}$ can be identical or different;

$R^4$, $R^5$, $R^6$, $R^7$, $R^8$, $R^9$ and $R^{11}$ are each hydrogen, alkyl, aryl, heteroaryl, alkynyl or alkenyl or a radical having a donor or acceptor action;

$R^{10}$ is alkyl, aryl, heteroaryl, alkynyl or alkenyl, or 2 radicals $R^{10}$ together form a fused-on ring which may optionally comprise at least one heteroatom, or $R^{10}$ is a radical having a donor or acceptor action;

with the group of the structure

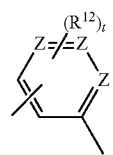

also being able to be joined via the aromatic basic skeleton or via one of the radicals $R^{12}$ to $R^4$ or $R^5$ or the carbon atom to which $R^4$ and $R^5$ are bound in the groups a and f, $R^8$ or the carbon atom to which $R^8$ is bound in the groups b and g, one of the radicals $R^{10}$ or one of the carbon atoms to which $R^{10}$ is bound in the groups c and h and $R^{11}$ or the carbon atom to which $R^{11}$ is bound in the groups d and i via a bridge which can have the following meanings:

alkylene, arylene, heteroarylene, alkynylene, alkenylene, $NR^{18}$, $PR^{19}$, $BR^{20}$, O, S, SO, $SO_2$, $SiR^{30}R^{31}$, CO, CO—O, O—CO and $(CR^{21}R^{22})_x$, where one or more nonadjacent $(CR^{21}R^{22})$ groups may be replaced by $NR^{18}$, $PR^{19}$, $BR^{20}$, O, S, SO, $SO_2$, $SiR^{30}R^{31}$, CO, CO—O, O—CO, where x is from 2 to 10;

and $R^{18}$, $R^{19}$, $R^{20}$, $R^{21}$, $R^{22}$, $R^{30}$, $R^{31}$ are each H, alkyl, aryl, heteroaryl, alkenyl, alkynyl;

where in the cases in which the group of the structure

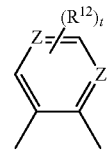

is linked via a bridge to the carbon atom to which $R^4$ and $R^5$ are bound (groups a and f), the carbon atom to which $R^8$ is bound (groups b and g), one of the carbon atoms to which $R^{10}$ is bound (groups c and h) or the carbon atom to which $R^{11}$ is bound (groups d and i), and the respective radical $R^4$ or $R^5$, $R^8$, one of the radicals $R^{10}$ and $R^{11}$ is replaced by a bond to the bridge;

v is from 0 to 4, where, when v is 0, the four carbon atoms of the aryl radical in formulae c and h which may optionally be substituted by $R^{10}$ bear hydrogen atoms;

$Y^3$ is hydrogen, an alkyl, aryl, heteroaryl, alkynyl or alkenyl radical

L is a monoanionic or dianionic ligand which may be monodentate or bidentate;

K is an uncharged monodentate or bidentate ligand;

n is the number of carbene ligands, with n being at least 1, and the carbene ligands in the complex of the formula I being able to be identical or different in the case of n>1;

m is the number of ligands L, with m being able to be 0 or ≥1 and the ligands L being able to be identical or different in the case of m>1;

o is the number of ligands K, with o being able to be 0 or ≥1 and the ligands K being able to be identical or different in the case of o>1;

where the sum n+m+o is dependent on the oxidation state and coordination number of the metal atom used and on the denticity of the ligands carbene, L and K and also on the charge on the ligands carbene and L, with the proviso that n is at least 1;

which comprises reaction of a ligand precursor selected from the group consisting of ligand precursors a'-j':

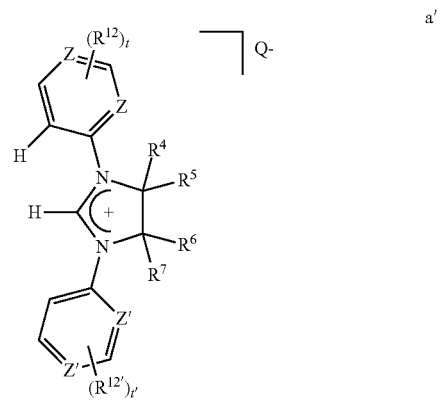

b'
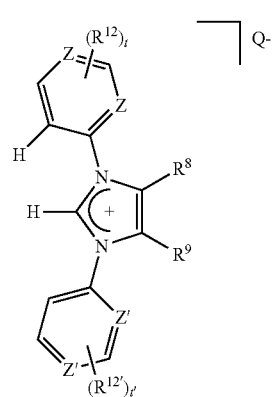
c'
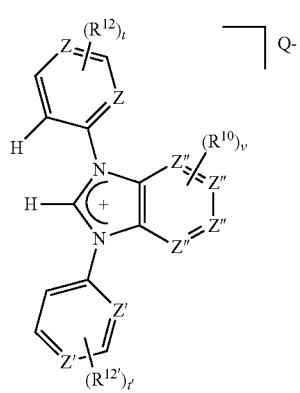
d'
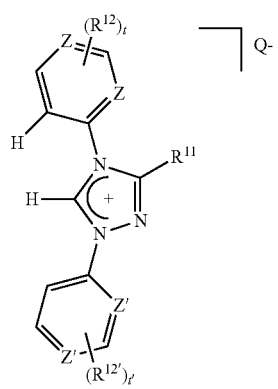
e'
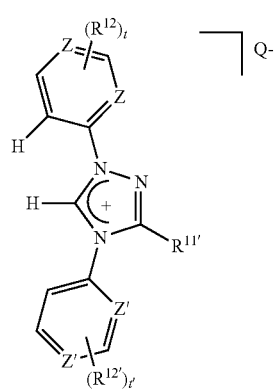
f'
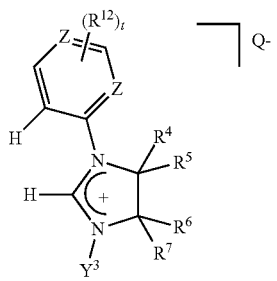
g'
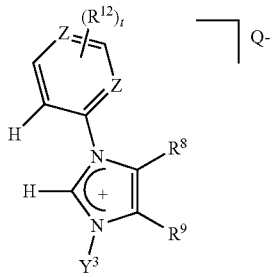
h'
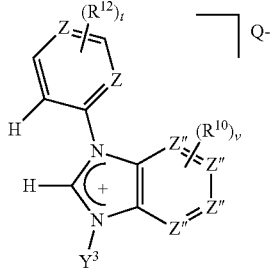
i'
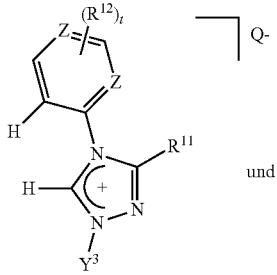
und
j'
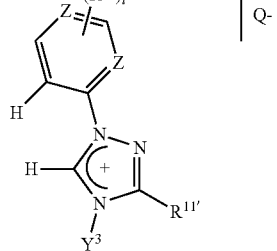
where
Q⁻ is a monoanionic counterion,
and
the further symbols in formulae a'-j' have the meanings given in respect of carbene ligands a-j,
wherein
the reaction comprises the use of a base and an auxiliary reagent selected from among salts of Ag, Hg, Sb, Mg, B and Al (route A) and the ligand precursor selected from the group consisting of ligand precursors a'-j' is (A) reacted with the base, a metal complex comprising at least one metal $M^1$ and the auxiliary reagent (route A); to give a cyclometallated carbene complex of the formula I.

2. The process according to claim 1, wherein
(A) the ratio of metal complex comprising at least one metal $M^1$, ligand precursor selected from the group consisting of ligands a'-j', base and auxiliary reagent is 1:1-10:1-10:0.5-15 per metal atom $M^1$ and number of carbene ligands n (route A).

3. The process according to claim 1, wherein the process is carried out in a solvent.

4. The process according to claim 1, wherein the process is carried out at from 60 to 200° C.

5. The process according to claim 1, wherein Ir is used as metal $M^1$.

6. The process according to claim 1, wherein the auxiliary reagent used according to route A is selected from among salts of Ag.

7. The process according to claim 1, wherein the base used in route A is selected from the group consisting of KHMDS, NaHMDS, LiHMDS, KO$^t$Bu, NaO$^t$Bu, LiO$^t$Bu, NaH, KOAc, NaOAc, LiOAc, NEt$_3$, BuLi, RMgHal, where R is alkyl, aryl, alkenyl, KOH, NaOH, LiOH, Cs$_2$CO$_3$, K$_2$CO$_3$, Na$_2$CO$_3$, Li$_2$CO$_3$, pyridine and DBU.

8. The process according to claim 1, wherein the auxiliary reagent used in route A is selected from among AgBF$_4$, AgNO$_3$, AgSbF$_6$, AgPF$_6$, AgAsF$_6$, AgSCN, AgOCN, Ag$_2$SO$_4$, AgClO$_4$, Ag(COOCF$_3$), and Ag(OTf).

9. The process according to claim 1, wherein ligand precursor a' is reacted with the base, said metal complex comprising at least one metal $M^1$ and the auxiliary reagent (route A) to give a cyclometallated carbene complex of the formula I.

10. The process according to claim 1, wherein ligand precursor b' is reacted with the base, said metal complex comprising at least one metal $M^1$ and the auxiliary reagent (route A) to give a cyclometallated carbene complex of the formula I.

11. The process according to claim 1, wherein ligand precursor c' is reacted with the base, said metal complex comprising at least one metal $M^1$ and the auxiliary reagent (route A) to give a cyclometallated carbene complex of the formula I.

12. The process according to claim 1, wherein ligand precursor d' is reacted with the base, said metal complex comprising at least one metal $M^1$ and the auxiliary reagent (route A) to give a cyclometallated carbene complex of the formula I.

13. The process according to claim 1, wherein ligand precursor e' is reacted with the base, said metal complex comprising at least one metal $M^1$ and the auxiliary reagent (route A) to give a cyclometallated carbene complex of the formula I.

14. The process according to claim 1, wherein ligand precursor f' is reacted with the base, said metal complex comprising at least one metal $M^1$ and the auxiliary reagent (route A) to give a cyclometallated carbene complex of the formula I.

15. The process according to claim 1, wherein ligand precursor g' is reacted with the base, said metal complex comprising at least one metal $M^1$ and the auxiliary reagent (route A) to give a cyclometallated carbene complex of the formula I.

16. The process according to claim 1, wherein ligand precursor h' is reacted with the base, said metal complex comprising at least one metal $M^1$ and the auxiliary reagent (route A) to give a cyclometallated carbene complex of the formula I.

17. The process according to claim 1, wherein ligand precursor i' is reacted with the base, said metal complex comprising at least one metal $M^1$ and the auxiliary reagent (route A) to give a cyclometallated carbene complex of the formula I.

18. The process according to claim 1, wherein ligand precursor j' is reacted with the base, said metal complex comprising at least one metal $M^1$ and the auxiliary reagent (route A) to give a cyclometallated carbene complex of the formula I.

19. The process according to claim 1, wherein cyclometallated carbene complex of formula I prepared is (mer)-tris[1-(4'-cyanophenyl)-3-methylbenzimidazol-2-ylidene-$C^2$, $C^{2'}$]iridium(III).

* * * * *